United States Patent
Takahashi et al.

(10) Patent No.: US 10,410,343 B2
(45) Date of Patent: Sep. 10, 2019

(54) IMAGE COMPUTING DEVICE, IMAGE COMPUTING METHOD, AND TOMOGRAPH

(71) Applicant: HITACHI, LTD., Tokyo (JP)

(72) Inventors: Hisashi Takahashi, Tokyo (JP); Taiga Goto, Tokyo (JP); Koichi Hirokawa, Tokyo (JP)

(73) Assignee: HITACHI, LTD., Tokyo (JP)

( * ) Notice: Subject to any disclaimer, the term of this patent is extended or adjusted under 35 U.S.C. 154(b) by 158 days.

(21) Appl. No.: 15/580,337

(22) PCT Filed: Jun. 22, 2016

(86) PCT No.: PCT/JP2016/068470
§ 371 (c)(1),
(2) Date: Dec. 7, 2017

(87) PCT Pub. No.: WO2017/006764
PCT Pub. Date: Jan. 12, 2017

(65) Prior Publication Data
US 2018/0165807 A1 Jun. 14, 2018

(30) Foreign Application Priority Data
Jul. 8, 2015 (JP) .................. 2015-137260

(51) Int. Cl.
*G06T 7/00* (2017.01)
*A61B 6/03* (2006.01)
(Continued)

(52) U.S. Cl.
CPC ............ *G06T 7/0012* (2013.01); *A61B 6/032* (2013.01); *A61B 6/5205* (2013.01); *A61B 6/583* (2013.01);
(Continued)

(58) Field of Classification Search
CPC ... G06T 11/003; G06T 11/006; G06T 7/0012; A61B 6/032
See application file for complete search history.

(56) References Cited

U.S. PATENT DOCUMENTS 7,831,097 B2 11/2010 Chen et al.
2007/0217566 A1 9/2007 Chen et al.
(Continued)

FOREIGN PATENT DOCUMENTS

JP 2007-244871 9/2007
JP 2015-80719 4/2015
(Continued)

OTHER PUBLICATIONS

International Search Report dated Sep. 20, 2016 in connection with PCT/JP2016/068470.
(Continued)

*Primary Examiner* — Utpal D Shah
(74) *Attorney, Agent, or Firm* — Cooper & Dunham LLP

(57) ABSTRACT

A reconstruction image is generated with a small number of updates, with the use of an iterative approximation method. A specified tomographic image of a subject is received, and a process is performed two or more times, where an update process is performed according to the iterative approximation method, using the tomographic image as an initial image and an update image is obtained. Then, an update vector corresponding to a difference between thus generated update images of the update process performed twice is multiplied by predetermined coefficients, so as to generate an estimated update vector. Using this vector, an update image is generated. Then, this update image is used as a new initial image, and a process is repeated where the update process is performed according to the iterative approxima-
(Continued)

tion method and an update image is obtained, thereby generating a tomographic image of the subject.

11 Claims, 11 Drawing Sheets

(51) Int. Cl.
  *G06T 5/00* (2006.01)
  *G06T 11/00* (2006.01)
  *G01R 33/48* (2006.01)
  *A61B 6/00* (2006.01)
  *G01R 33/56* (2006.01)
  *A61B 6/06* (2006.01)

(52) U.S. Cl.
  CPC .......... *G01R 33/4812* (2013.01); *G06T 5/003* (2013.01); *G06T 11/006* (2013.01); *A61B 6/06* (2013.01); *A61B 6/4035* (2013.01); *G01R 33/5608* (2013.01); *G06T 2211/424* (2013.01)

(56) References Cited

U.S. PATENT DOCUMENTS

| | | | | |
|---|---|---|---|---|
| 2009/0262996 | A1* | 10/2009 | Samsonov | G01R 33/4818 382/130 |
| 2012/0063658 | A1* | 3/2012 | Leroux | G06T 11/006 382/131 |
| 2013/0177132 | A1 | 7/2013 | Takahashi et al. | |
| 2013/0243299 | A1* | 9/2013 | Goto | G06T 11/006 382/131 |
| 2014/0369463 | A1* | 12/2014 | Thibault | G01N 23/046 378/19 |
| 2015/0086097 | A1* | 3/2015 | Chen | G06T 11/008 382/131 |
| 2015/0117732 | A1 | 4/2015 | Zamyatin et al. | |
| 2015/0297165 | A1 | 10/2015 | Tanaka et al. | |
| 2016/0015350 | A1* | 1/2016 | Chang | A61B 6/5258 250/362 |
| 2016/0055658 | A1* | 2/2016 | Liang | G06T 11/006 382/131 |
| 2017/0231581 | A1* | 8/2017 | Sheng | A61B 6/03 382/131 |
| 2018/0068467 | A1* | 3/2018 | Wang | A61B 6/032 |

FOREIGN PATENT DOCUMENTS

| | | |
|---|---|---|
| WO | WO 2012/050149 A1 | 4/2012 |
| WO | WO 2014/084291 A1 | 6/2014 |

OTHER PUBLICATIONS

S. Ahn et. al., "Globally Convergent Image Reconstruction for Emission Tomography Using Relaxed Ordered Subsets Algorithms," IEEE. Trans. Med. Imag:, vol. 22, No. 5, pp. 613-626, 2003.

A. Beck et. al., "A Fast Iterative Shrinkage-Thresholding Algorithm for Linear Inverse Problems," SIAM J. Imaging Sci., vol. 2, No. 1, pp. 183-202, 2009.

D. Kim et. al., "Combining Ordered Subsets and Momentum for Accelerated X-ray CT Image Reconstruction," IEEE. Trans. Med. Imag., vol. 34, No. 1, pp. 167-178, 2015.

H. Nien et. al., "Fast X-ray CT Image Reconstruction Using the Linearized Augmented Lagrangian Method with Ordered Subsets," Technical report, [online], Feb. 18, 2014, arXiv e-print [Searched on Jul. 8, 2015], Internet Web page <URL:http://arxiv.org/abs/1402.4381>.

T. Goldstein et. al., "The split Bregman method for L1-regularized problem," SIAM J. Imaging Sci., vol. 2, No. 2, pp. 323-343, 2009.

S. Ramani et. al., "A Splitting-Based Iterative Algorithm for Accelerated Statistical X-Ray CT Reconstruction," IEEE. Trans. Med. Imag., vol. 31, No. 3, pp. 677-688, 2012.

H. Nien et. al., "Fast Splitting-Based Ordered-Subsets X-Ray CT Image Reconstruction," Proc of the third international conference on image formation in X-ray computed tomography, pp. 291-294, 2014.

* cited by examiner

IMAGE COMPUTING DEVICE, IMAGE COMPUTING METHOD, AND TOMOGRAPH

TECHNICAL FIELD

The present invention relates to a technique for image quality improvement of an image computing device such as a CT (Computed Tomography) device and a magnetic resonance imaging (hereinafter, referred to as MRI) device, and more particularly, it relates to an image computing device for providing a high-speed iterative approximation method.

BACKGROUND ART

As medical-use tomographic imaging devices for imaging a human body non-invasively, CT devices and MRI devices are widely utilized. Aiming at precision-enhancement in imaging and increasing the number of cases that are diagnosable, research and development have been carried out as to an element technology of a tomographic imaging device such as the CT device and MRI device. It is known that image reconstruction methods of the imaging device such as the CT device and MRI device fall into two broad categories, analytical reconstruction method and algebraic reconstruction method. Examples of the analytical reconstruction method are Fourier transform method, filtered back projection method, and convolution integral method. On the other hand, an example of the algebraic reconstruction method is an iterative reconstruction method.

In recent years, aiming at improvement of image quality, there have been actively suggested, methods that apply the iterative approximation method to an image reconstruction algorithm. For example, it is disclosed in the paragraphs 0005, and 0014 to 0019 of the patent document 1, describing a method that employs as the iterative approximation method (iterative method), an objective function (evaluation function) including a data fidelity term which enforces similarity between measured sinogram and a forward projection of an reconstruction image, and a regularization term which enforces a prior knowledge about a signal (e.g. smooth curved surface with sharp edges).

PRIOR ART DOCUMENT

Patent Document

Patent Document 1:
Japanese Unexamined Patent Application Publication No. 2007-244871

Non Patent Document

Non Patent Document 1:
S. Ahn et. al., "Globally Convergent Image Reconstruction for Emission Tomography Using Relaxed Ordered Subsets Algorithms," IEEE. Trans. Med. Imag., vol. 22, no. 5, pp. 613-626, 2003
Non Patent Document 2:
A. Beck et. al., "A Fast Iterative Shrinkage-Thresholding Algorithm for Linear Inverse Problems," SIAM J. Imaging Sci., vol. 2, no. 1, pp. 183-202, 2009
Non Patent Document 3:
D. Kim et. al., "Combining Ordered Subsets and Momentum for Accelerated X-ray CT Image Reconstruction," IEEE. Trans. Med. Imag., vol. 34, no. 1, pp. 167-178, 2015
Non Patent Document 4:
H. Nien et. al., Fast X-ray CT Image Reconstruction Using the Linearized Augmented Lagrangian Method with Ordered Subsets," Technical report, [online], 18 Feb. 2014, arXiv e-print [Searched on Jul. 8, 2015], Internet Web page <URL:http://arxiv-org/abs/1402.4381>
Non Patent Document 5:
T. Goldstein et. al., "The split Bregman method for L1-regularized problem," SIAM J. Imaging Sci., vol. 2, no. 2, pp. 323-343, 2009
Non Patent Document 6:
S. Ramani et. al., "A Splitting-Based Iterative Algorithm for Accelerated Statistical X-Ray CT Reconstruction," IEEE. Trans. Med. Imag., vol. 31, no. 3, pp. 677-688, 2012
Non Patent Document 7:
H. Nien et. al., "Fast Splitting-Based Ordered-Subsets X-Ray CT Image Reconstruction," Proc of The third international conference on image formation in X-ray computed tomography, pp. 291-294, 2014

DISCLOSURE OF THE INVENTION

Problems to be Solved by the Invention

In the image reconstruction algorithm employing a conventional iterative approximation method, the objective function (evaluation function) cannot converge without a large number of iterations (updates), and thus, iterations (updates) exceeding dozens of times (hundreds of times, in some instances) have been required. Accordingly, there has been a problem that it is difficult to generate a reconstruction image within a practical calculation time, when the iterative approximation method is used in an arithmetic unit of a tomographic imaging device, such as generally used CT device and MRI device.

An object of the present invention is to generate a reconstruction image where only a small number of updates are required, with the use of the iterative approximation method.

Means for Solving the Problems

In order to achieve the object above, an image computing device of the present invention comprises, a first iterative approximation processor configured to receive a specified tomographic image of a subject, and to perform a process two or more times, where an update process is performed according to the iterative approximation method, using the tomographic image as an initial image and an update image is obtained, an estimated update image generator configured to generate an estimated update vector obtained by multiplying an update vector by a predetermined coefficient, the update vector corresponding to a difference between the update images of the update process performed twice, generated by the first iterative approximation processor, and to generate an estimated update image by using the estimated update vector, and a second iterative approximation processor configured to repeat a process where the update process is performed according to the iterative approximation method and an update image is obtained, using the estimated update image as a new initial image, thereby generating a tomographic image of the subject.

Advantage of the Invention

According to the present invention, it is possible to reduce the number of updates required for convergence of the image reconstruction algorithm using the iterative approximation method, and a reconstruction image can be generated in a short calculation time.

BEST MODE FOR CARRYING OUT THE INVENTION

Figure 1:
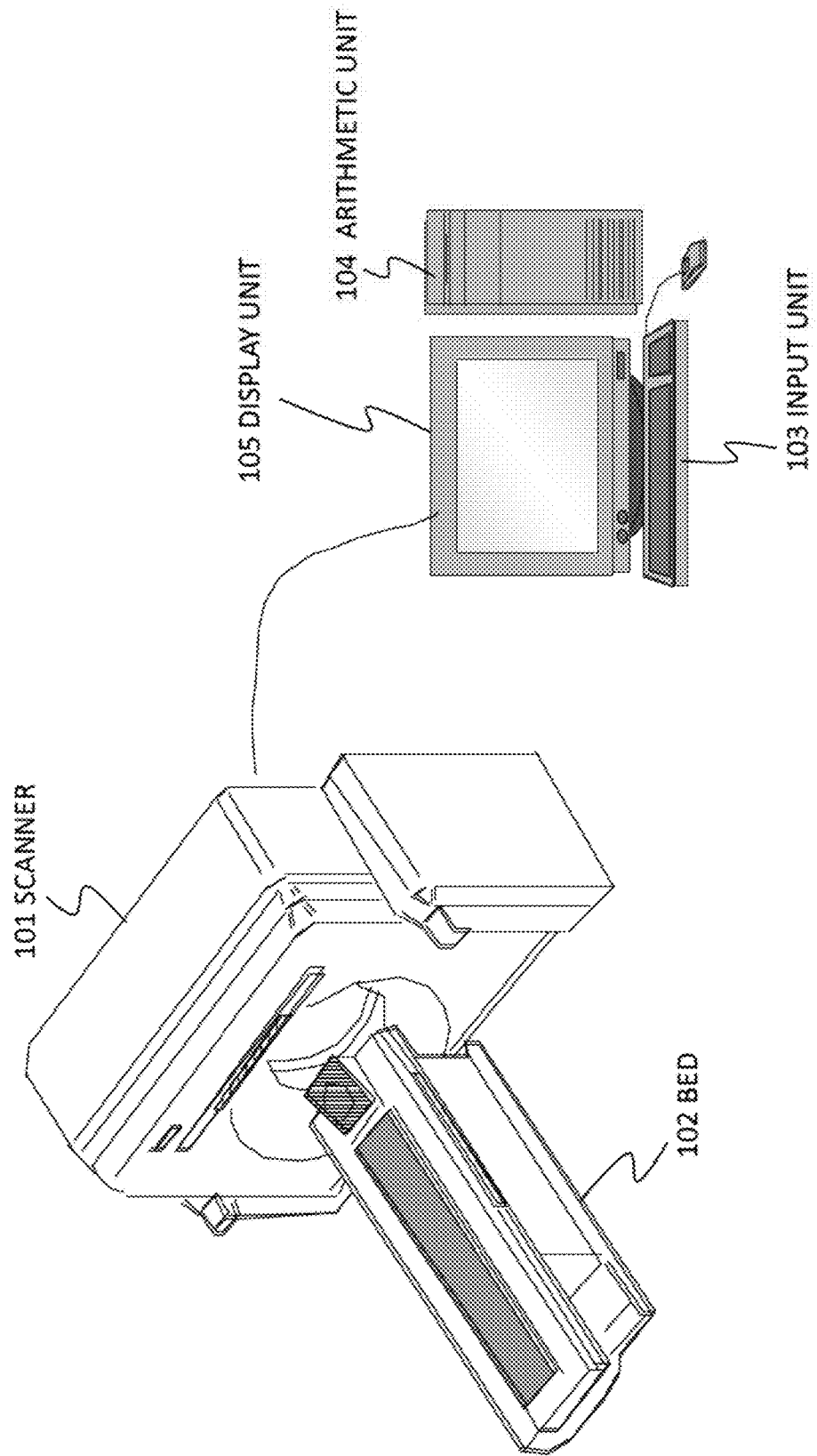
FIG. 1 illustrates an external overview of a CT device according to a first embodiment.

Embodiments of the present invention will now be described, with reference to the accompanying drawings. Hereinafter, in all the figures illustrating the embodiments of the present invention, elements with an identical function are labeled with the same reference numeral, and they will not be redundantly explained.

First Embodiment

Figure 2:
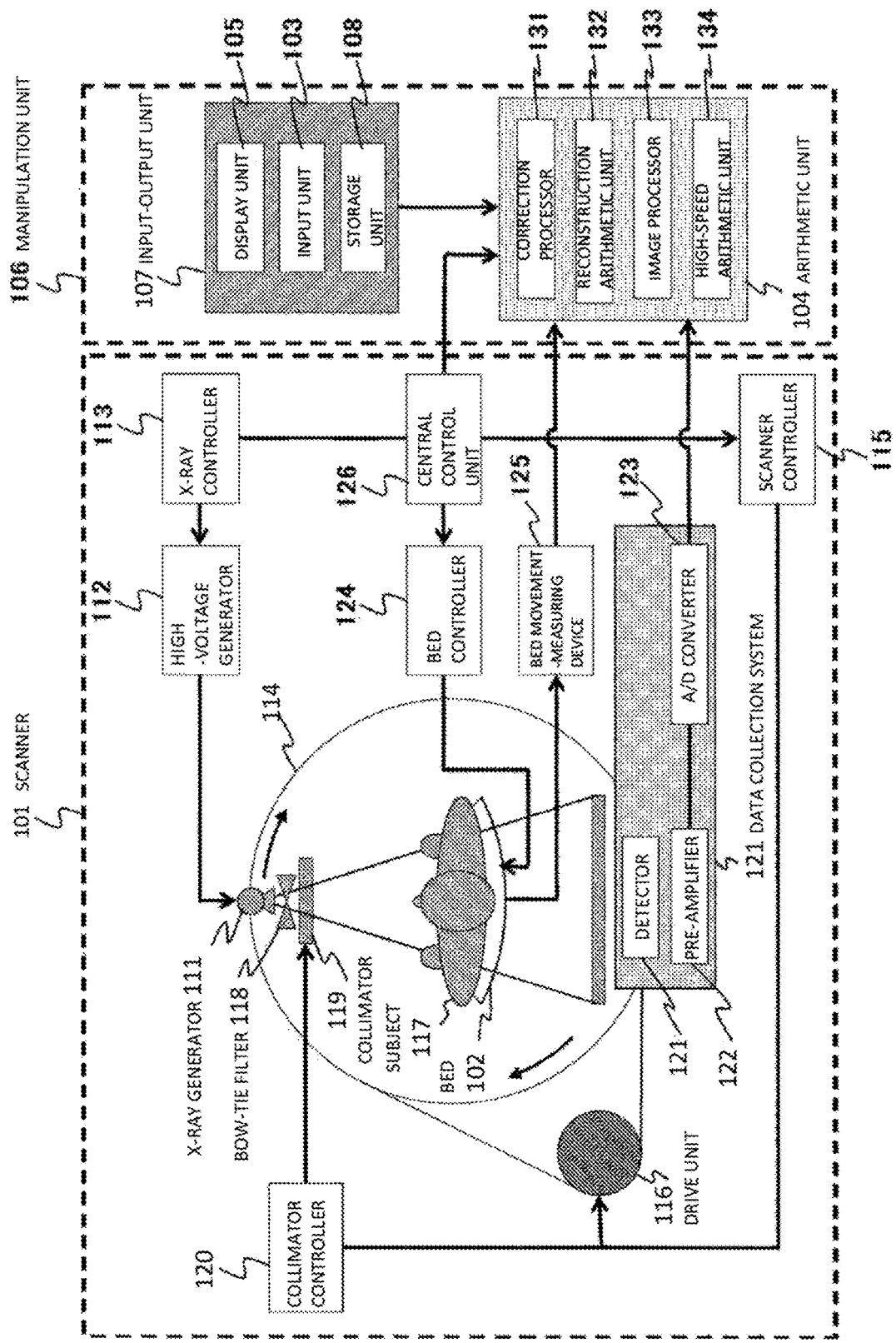
FIG. 2 is a block diagram showing a configuration of the CT device according to the first embodiment.

FIG. 1 is an external overview of a CT device relating to the present embodiment, and FIG. 2 illustrates an overall configuration of the CT device.

As illustrated in FIG. 1, the CT device is provided with a scanner 101 used for imaging, a bed 102 for moving a subject placed thereon, an input unit 103 comprising a mouse, a keyboard, and the like, for accepting an operator's inputs of parameters used for measurement and reconstruction, such as bed moving-speed information and a position for reconstruction, an arithmetic unit 104 for processing measured data outputted from the scanner 101, and a display unit 105 for displaying a reconstruction image.

As shown in FIG. 2, the scanner 101 incorporates an X-ray generator 111, a high-voltage generator 112, an X-ray controller 113, a data collection system 129, a scanner controller 115, and a central control unit 126. The high-voltage generator 112 generates predetermined current and high voltage under the control of the X-ray controller 113, and supplies the high voltage to the X-ray generator 111. Accordingly, the X-ray generator 111 generates X-rays.

The X-ray generator 111 and a detector 121 are mounted on a disk 114 provided with an aperture for putting a subject 117 into the center thereof. The disk 114 is provided with a drive unit 116 for rotationally driving the disk 114. In addition, the disk 114 is further provided with a Bow-tie filter 118 and a collimator 119 at positions where X-rays generated by the X-ray generator 111 pass through.

The collimator 119 is connected to a collimator controller 120. The scanner controller 115 is connected to the drive unit 116 and the collimator controller 120, so as to control rotation and stop of the dish 114, and also to control the aperture of the collimator 119.

The detector 121 is connected to a pre-amplifier 122 and an A/D converter 123, in this order. The pre-amplifier 122 amplifies an output from the detector 121, and then, the A/D converter 123 converts the amplified output to digital signals and transfers the digital signals to the arithmetic unit 104. The pre-amplifier 122 and the A/D converter 123 are also mounted on the disk 114. The pre-amplifier and the A/D converter 123 constitute the data collection system 129.

The bed 102 incorporates a bed drive unit for moving the bed 102 with respect to the disk 114. The bed drive unit is connected to a bed controller 124 for controlling a drive amount thereof, and a bed movement-measuring device 125.

The display unit 105 and the input unit 103 configure an input-output unit 107. The input-output unit 107 is also provided with a storage unit 108. As for the arithmetic unit 104, it is provided with a correction processor 131, a reconstruction arithmetic unit 132, an image processor 133, and a high-speed arithmetic unit 134. The input-output unit 107 and the arithmetic unit 104 constitute a manipulation unit 106.

Operations of each unit will now be described. When an operator enters from the input unit 103 in the manipulation unit 106, imaging conditions (including a bed moving speed, tube current, tube voltage, and a slice position), and reconstruction parameters (including a region of interest, a reconstruction image size, a back-projection phase width, a reconstruction filter function, and a thickness of image in a body axis direction), a central control unit 126 outputs control signals necessary for imaging, on the basis of the instructions, to the X-ray controller 113, the bed controller 124, and the scanner controller 115.

Then, when the operator manipulates the input unit 103 and outputs an imaging start signal, the imaging starts. When the imaging starts, the X-ray controller 113 transmits a control signal to the high-voltage generator 112, then, high voltage is applied to the X-ray generator 111, and the subject 117 is irradiated with X-rays from the X-ray generator 111. Simultaneously, the control signal is transmitted from the scanner controller 115 to the drive unit 116, so as to turn the disk 114. Accordingly, the X-ray generator 111, the detector 121, the pre-amplifier 122, and the like, circulate around the subject. On the other hand, according to the control by the bed controller 124, the bed 102 placing the subject 117 thereon moves in parallel with the body axis direction, or stops the motion.

A shape of X-ray beams of the X-rays emitted from the X-ray generator 111 is formed by the Bow-tie filter 118, its irradiation area being limited by a collimator 119, and then applied to the subject 117. The X-rays are absorbed (made to attenuate) within tissue of the subject 117, pass through the subject 117, and detected by the detector 121, at sampling intervals being defined with respect to a rotation direction. The unit of data collection in the rotation direction as described above is referred to as "view". It is to be noted that the detector 121 has a configuration where detection elements are arranged two-dimensionally, and a line of the elements in the rotation direction is referred to as "channel" and a direction orthogonal thereto is referred to as "column". Then, collected data is identified by the view, channel, and column.

The X-rays detected by each of the detection elements of the detector 121 are converted into current, amplified by the pre-amplifier 122, converted into digital signals by the A/D converter 123, and then outputted to the arithmetic unit 104.

The correction processor 131 in the arithmetic unit 104 performs following processes on the digital signals from the A/D converter 123, such as an offset correction process for correcting output offsets due to dark current from the detection elements, an air correction process, a reference correction process, a logarithmic transformation, and a phantom calibration process for reducing beam hardening effects. Data after correction is stored as actual measured projection data, in the storage unit 108 within the input-output unit 107.

The reconstruction arithmetic unit 132 performs an image reconstruction process on the actual measured projection data. The reconstruction arithmetic unit 132 executes the image reconstruction process, on the basis of the analytical reconstruction method (including the Fourier transform method, filtered back projection method, and convolution integral method, for instance) where computations are generally completed within a short time. The reconstruction image is stored in the storage unit 108 in the input-output unit 107, and displayed on the display unit 105 as a CT image. In addition, when the operator instructs via the input unit 103 to perform a process on the displayed CT image, such as a process for modifying a displayed cross section, the image processor 133 executes thus instructed process.

The high-speed arithmetic unit 134 further processes the reconstruction image according to an iterative approximation method that is an algebraic reconstruction method, so as to generate an image with a higher degree of precision, the reconstruction image having been generated by the reconstruction arithmetic unit 132 according to the analytical reconstruction method.

Figure 3:
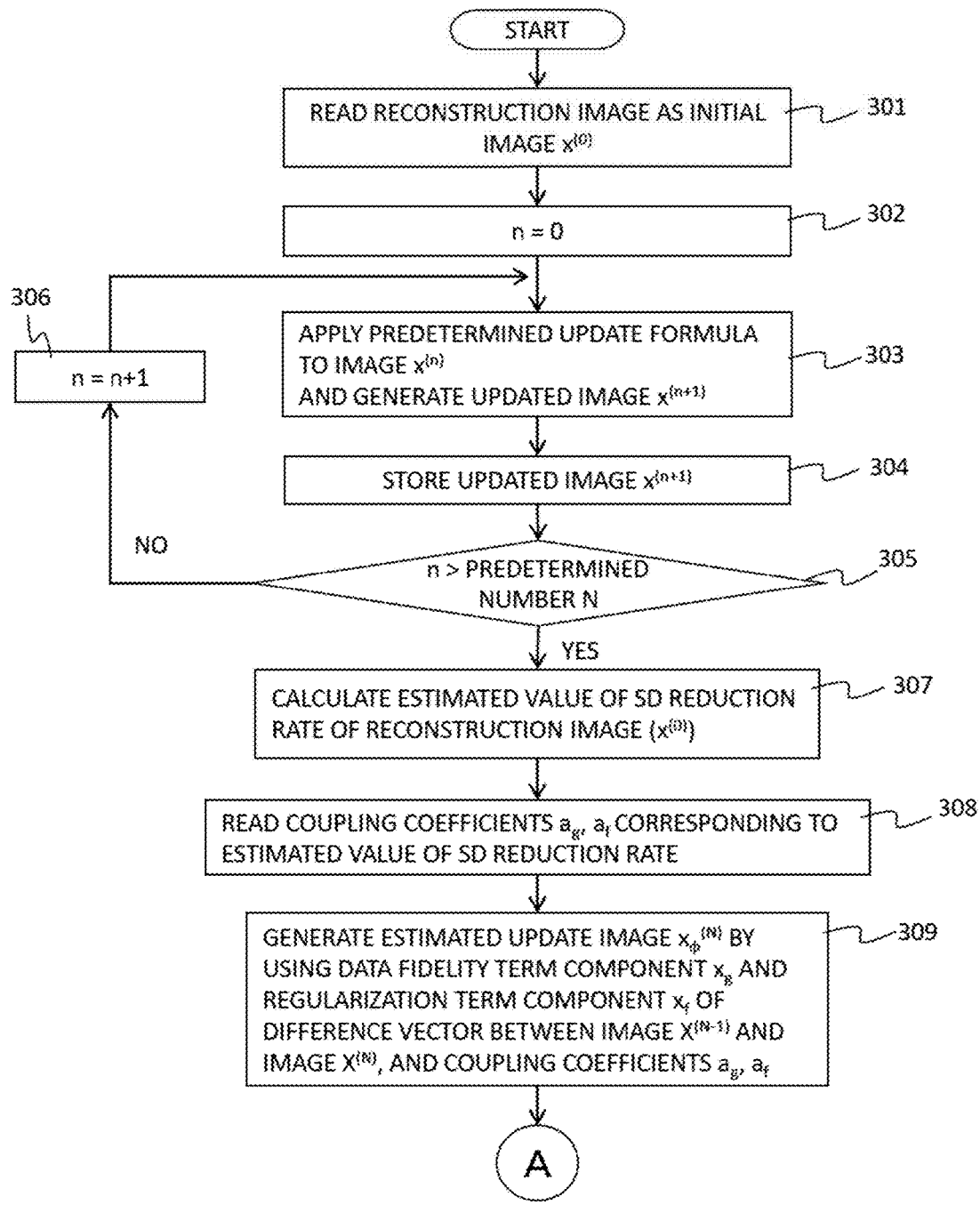
FIG. 3 is a flowchart showing an operation of a high-speed computing device of the CT device according to the first embodiment.
Figure 4:
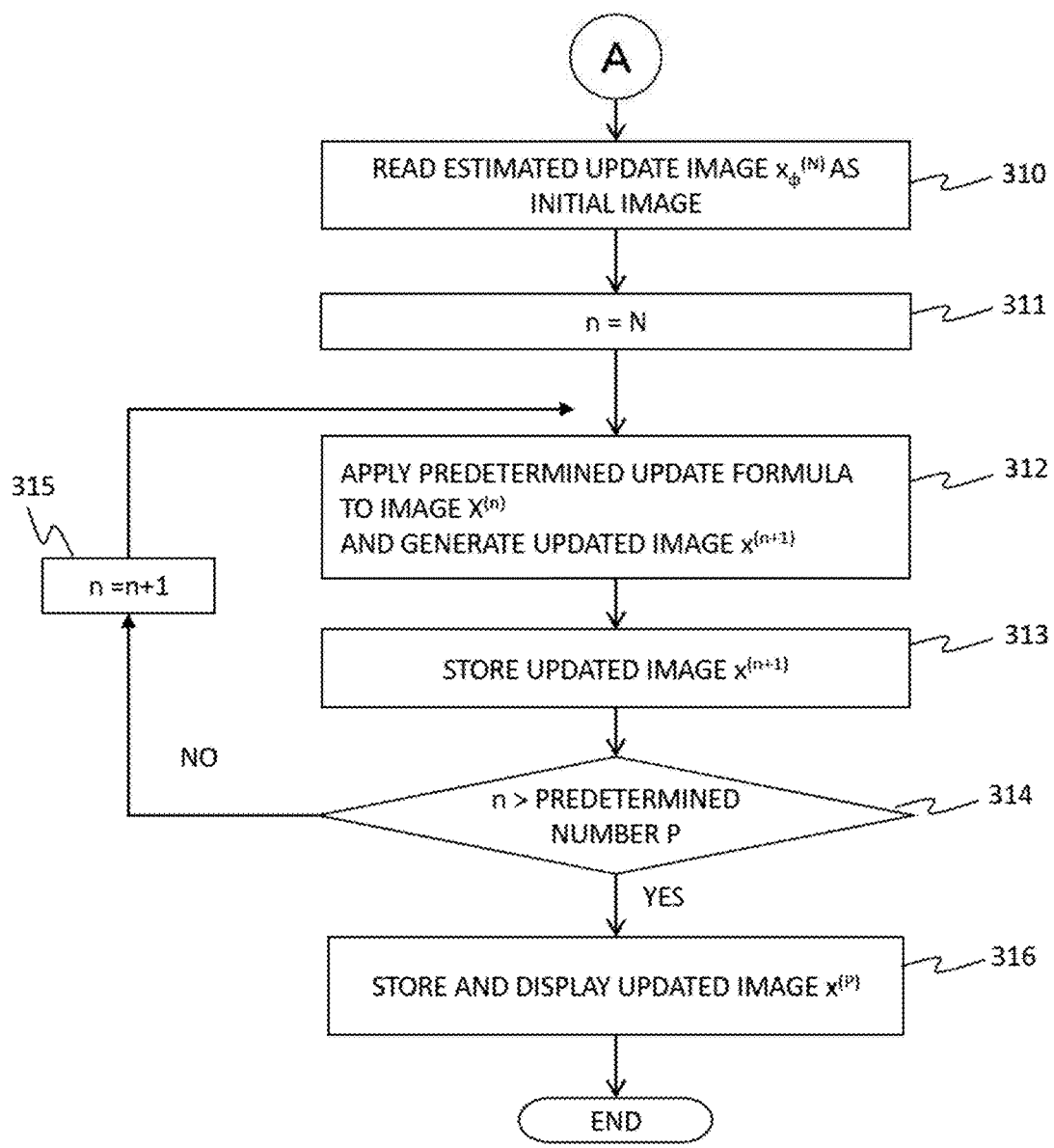
FIG. 4 is a flowchart showing an operation of the high-speed computing device of the CT device according to the first embodiment.

Specifically, the high-speed arithmetic unit 134 incorporates a CPU (Central Processing Unit) and a memory (both are not illustrated), and the CPU reads and executes programs stored in advance in the memory, whereby an image is generated according to the iterative approximation method, through the operations as shown in the flowcharts of FIGS. 3 and 4. Alternatively, other configurations may be applicable, such as a configuration employing a GPU (Graphics Processing Unit) chip instead of the CPU, and a configuration where an integrated circuit (hardware) such as FPGA (Field-Programmable Gate Array) and ASIC (Application Specific Integrated Circuit) performs the computation of the iterative approximation method.

An overview of the operation of the high-speed arithmetic unit 134 will now be described with reference to the flowcharts of FIGS. 3 and 4, and the conceptual diagrams of FIGS. 5 and 6.

The high-speed arithmetic unit 134 sets as an initial image $x^{(0)}$, the reconstruction image generated by the reconstruction arithmetic unit 132, and performs an image update (iterative) operation according to the iterative approximation method, a predetermined number of times N (N≥2, e.g., N=3), whereby updated images $x^{(1)}$ to $x^{(N)}$ are obtained (e.g., $x^{(1)}$, $x^{(2)}$, and $x^{(3)}$) (see steps 301 to 306, and FIG. 5(a)). This is referred to as a first iterative approximation process.

In the first iterative approximation process, an update formula used for the update (iterative) operation includes both a data fidelity term and a regularization term. The data fidelity term is a term for estimating similarity between actual measured projection data collected by the data collection system 129, and forward projection data obtained by applying forward projection to the reconstruction image. The regularization term is a term for estimating the reconstruction image on the basis of prior knowledge as to the generated image, and it operates here for enforcing that the image is a flat image with less spatial variation in pixel values.

Next, the high-speed arithmetic unit 134 generates an estimated update vector that is obtained through multiplication by a predetermined coefficient, of the update vector $x_\varphi(N-1, N)$ corresponding to a difference vector between two obtained updated images $x^{(N)}$ and $x^{(N-1)}$ (e.g., $x^{(3)}$ and $x^{(2)}$), and then generates an estimated update image by using this vector. Specifically, in the update vector $x_\varphi(N-1, N)$, a vector component $x_g(N-1, N)$ originating from the data fidelity term and a vector component $x_f(N-1, N)$ originating from the regularization term are calculated, and those vector components are multiplied, respectively by predetermined coefficients (coupling coefficients) $a_g$ and $a_f$, and added together, thereby obtaining the estimated update vector. Then, thus obtained vector is used to generate the estimated update image $x_\varphi^{(N)}$ (see steps 307 to 309, and FIGS. 5(b) and 6(a)). Accordingly, the estimated update image $x_\varphi^{(N)}$ approximating the image after performing multiple update operations can be obtained, just by a single calculation.

Next, the high-speed arithmetic unit 134 sets thus calculated estimated update image $x_\varphi^{(N)}$ as an initial image, and performs the image update (iterative) operation for a predetermined number of times, according to the iterative approximation method, so as to obtain an updated image $x^{(P)}$ (a tomographic image of the subject) (see steps 310 to 315, and FIG. 6(b)). This is referred as a second iterative approximation process. Then, the updated image $x^{(N)}$ is subjected to operations such as being displayed (step 316).

In the present embodiment, the estimated update vector is obtained by multiplying the update vector by the coupling coefficients, and the estimated update image is obtained through computations using this estimated update vector, thereby achieving elimination of multiple update operations. In particular, a vector component $x_g(N-1, N)$ originating from the data fidelity term, and a vector component $x_f(N-1, N)$ originating from the regularization term are calculated, and those vector components are multiplied by the coupling coefficients, respectively. Compared to the case of the comparative example as shown in FIG. 7 where only the iterative approximation process is performed, convergence (or asymptotic approach) to an optimum solution x* can be achieved, through less number of update operations as shown in FIG. 6(b). Therefore, this enables high-speed generation of a highly precise image, by using the iterative approximation method.

Detailed description will now be provided, with reference to the flowcharts as shown in FIGS. 3 and 4.

In step 301, the high-speed arithmetic unit 134 reads the reconstruction image generated by the reconstruction arithmetic unit 132 from the storage unit 108, and sets this reconstruction image as the initial image $x^{(0)}$. Then, a predetermined update formula is applied to the initial image $x^{(0)}$, and an updated image $x^{(1)}$ is generated (steps 302 and 303). The update formula to be used includes both the data fidelity term and the regularization term. More specifically, the formula to be used satisfies the following conditions A and B.

A) Evaluation function includes both the data fidelity term and the regularization term; and B) Both in the condition A are used simultaneously (at the same timing) upon updating an image.

By way of example, in the present embodiment, the update formula described in the Non Patent Document 1 is employed.

Specific update formula is given by formula 1. It is to be noted that $x^{(n)}$ indicates the $n^{th}$ updated image, and $x^{(n-1)}$ indicates the $(n-1)^{th}$ updated image. In the following, $x^{(n)}$ will also be referred to as an image vector. A starting point of the image vector corresponds to a point where all the pixel values are zero (FIGS. 5, 6, and 7).

[Formula 1]

$$x^{(n)} = [x^{(n-1)} - \lambda_n D^{-1} \nabla \phi(x^{(n-1)})]_+ \quad (1)$$

In formula 1, the first derivative of the evaluation function $\phi(x)$ is represented by $\nabla\phi(x)$. $\lambda_n$ is a relaxation coefficient for adjusting a degree of updating, and it is predetermined with respect to each update count n. D is Hessian matrix of the evaluation function $\phi(x)$, but it is also possible to employ Lipschitz constant of $\phi(x)$. An example described in the Non Patent Document 2 may be employed as "D" where the Lipschitz constant of $\phi(x)$ is used.

In this example here, the evaluation function $\phi(x)$ is expressed by formula 2, being a sum of the data fidelity term $g(x)$ and the regularization term $f(x)$. The data fidelity term $g(x)$ restricts the state of an image obtained from actual measured projection data. That is, formula 3 is used, which evaluates similarity between the actual measured projection data collected by the data collection system 129 and the forward projection data obtained by applying forward projection to the reconstruction image. For the regularization term $f(x)$, formula 4 for evaluating smoothness between adjacent pixels is used. As the data fidelity term $g(x)$ and the regularization term $f(x)$ become smaller values, the closer becomes an optimum image x, and higher evaluation can be obtained (i.e., a value of the evaluation function $\phi(x)$ becomes smaller).

[Formula 2]

$$\Phi(x) = g(x) + f(x) \quad (2)$$

[Formula 3]

$$g(x) = \|Ax - y\|_W \quad (3)$$

[Formula 4]

$$f(x) = \sum_{k=1}^{K} \beta_k \sum_{j=1}^{J} \xi_{jk} \psi([C_k x]_j) \quad (4)$$

In formula 3, y is a vector of the actual measured projection data collected by the data collection system 129. A is a transformation matrix that is used for transforming the image to projection data. W is a matrix having as a diagonal component, a weight factor that is obtained by digitalizing statistical fluctuation of the actual measured projection data y.

In formula 4, k is an index indicating a direction of an adjacent pixel viewed from a target pixel of the image x, and K is a total sum of the directions. By way of example, when adjacent 26 pixels are targeted in a three-dimensional image, K becomes 13, avoiding redundancy. $\beta_k$ is an optional parameter that determines regularization strength in the k-direction, and $C_k$ is a matrix for extracting the adjacent elements of an image vector. In addition, a pixel index is represented by $j=\{1, \ldots, J\}$. $\xi_{jk}$ is a weight factor between the pixel j and k, and it is decided by a reciprocal number of the distance between the pixels, for instance. $\psi$ is a potential function, and a continuous function being differentiable everywhere, such as Huber function and Fair function, is used as the potential function.

In the example here, the data fidelity term $g(x)$ and the regularization term $f(x)$ are represented by formulas 3 and 4 described above. However, the present embodiment is not limited to those formulas 3 and 4. Any desired function can be used, as far as the function allows the first derivative functions $\nabla g(x)$ and $\nabla f(x)$ to be obtained by calculation. The update formula is not limited to formula 1 as described above, and any desired formula can be employed.

When the updated image $x^{(1)}$ is generated from the image $x^{(0)}$ after one-time update according to step 303, the updated image $x^{(1)}$ is stored in the storage unit 108. The update operations in steps 303 and 304 are repeated until the update count reaches a predetermined number N (steps 305 and 306). Then, in the storage unit 108, the updated images $x^{(1)}$ to $x^{(N)}$ (e.g., $x^{(1)}$, $x^{(2)}$, and $x^{(3)}$) are stored. According to the procedures so far, the first iterative approximation process is completed (steps 301 to 305).

Figure 5:
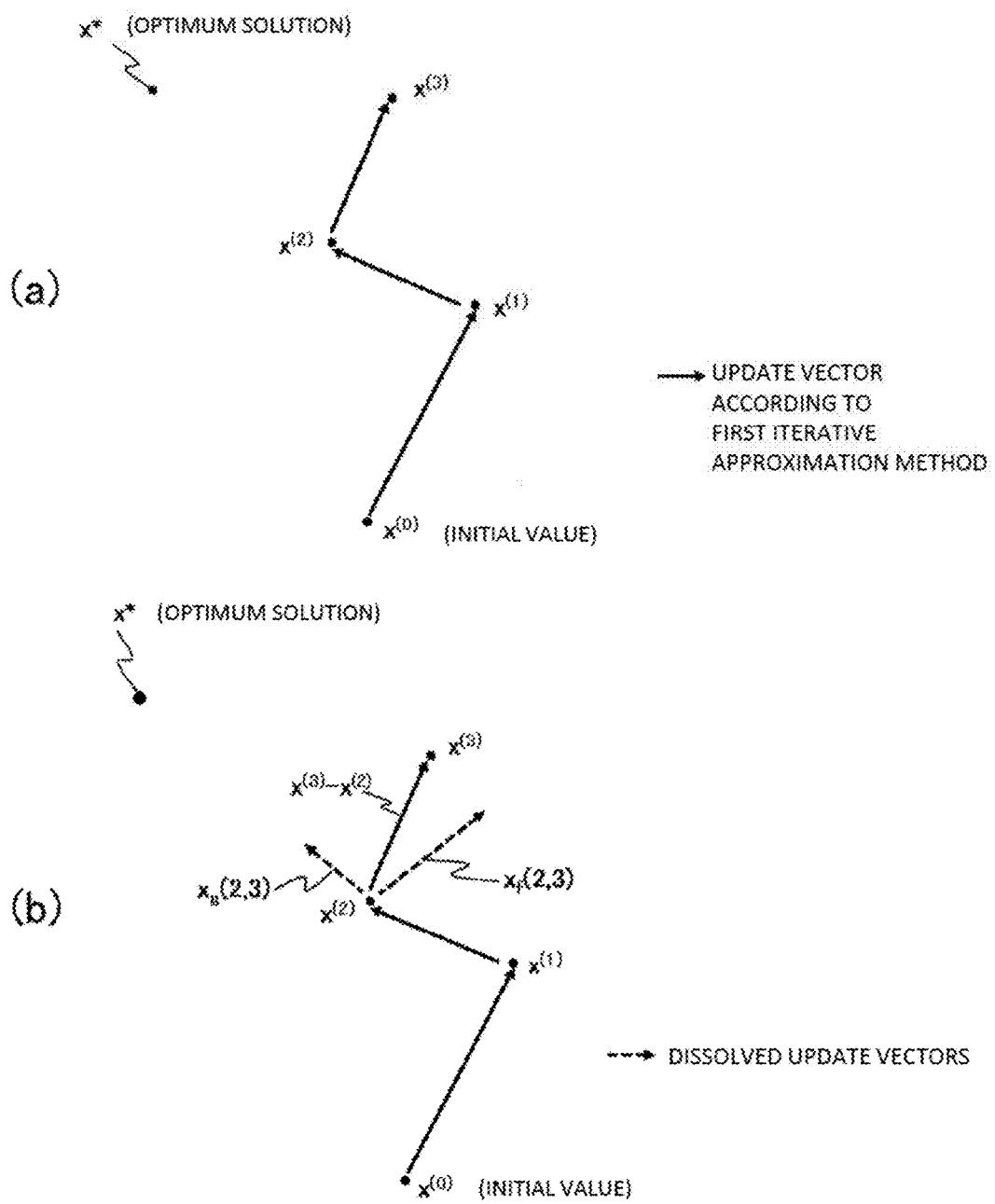
FIG. 5(a) illustrates an image (image vector) obtained by a first iterative approximation process of the first embodiment, and its update vector.
FIG. 5(b) illustrates the update vector is resolved into a vector component.
Figure 6:
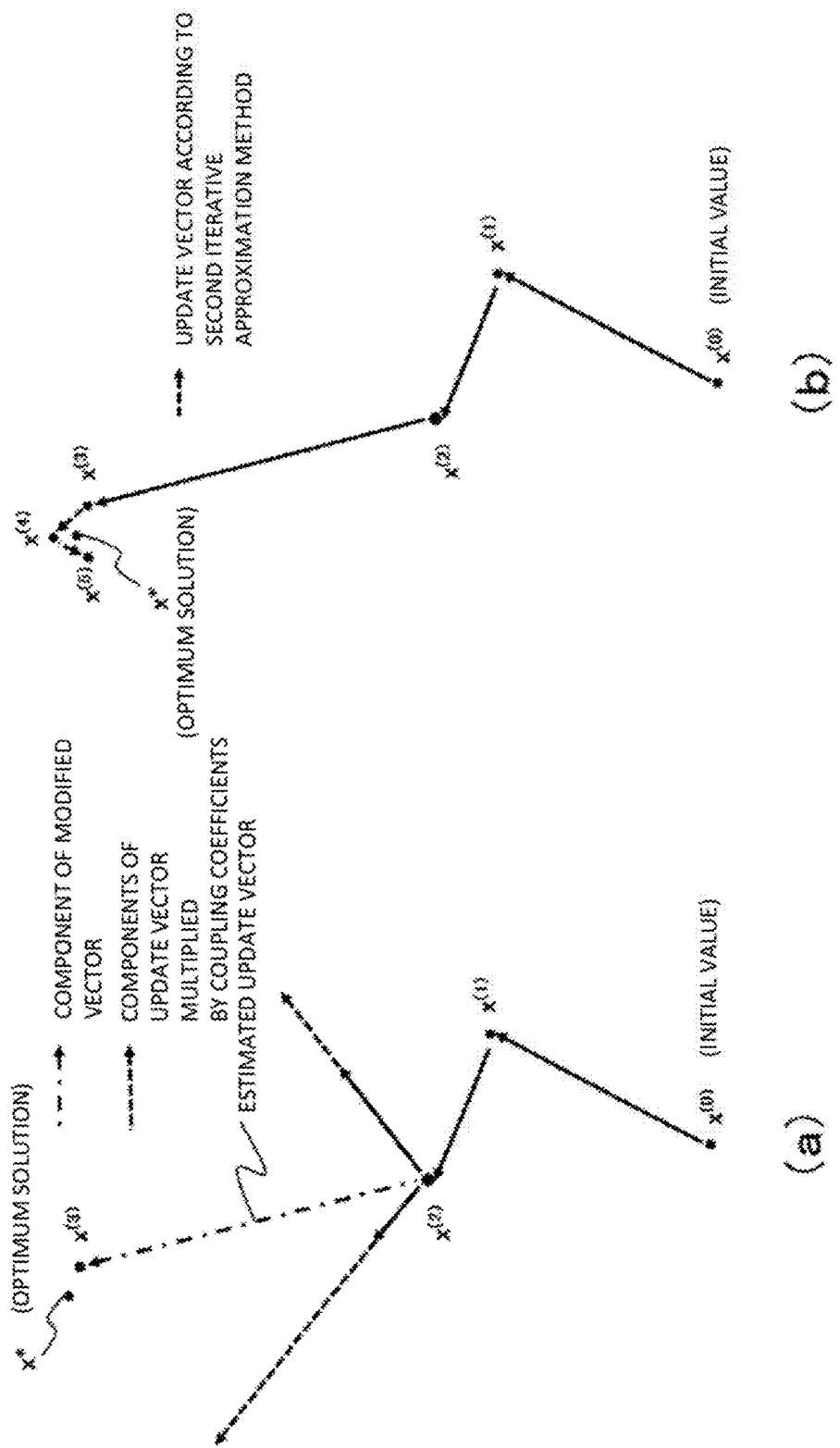
FIG. 6(a) illustrates that the update vector is multiplied by coefficients to obtain an estimated update vector.
FIG. 6(b) illustrates an image (image vector) obtained by a second iterative approximation process from the image (image vector) obtained by using the estimated update vector, and its update vector.
Figure 7:
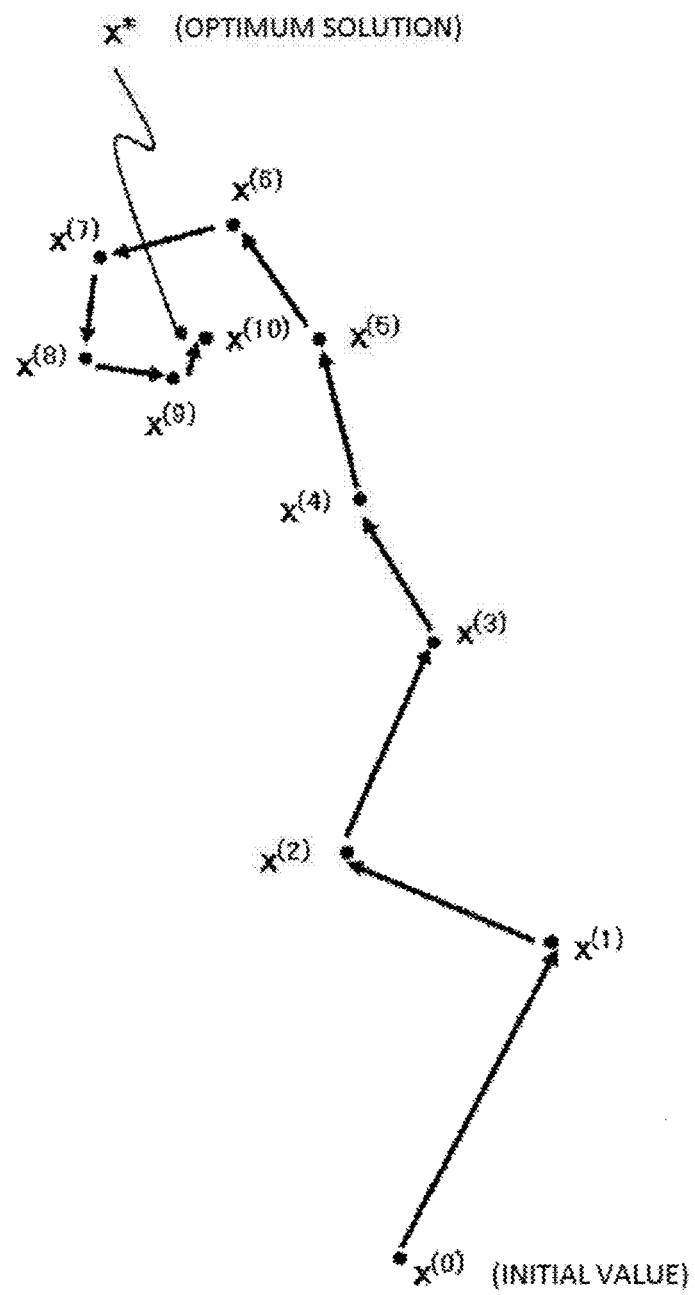
FIG. 7 illustrates an image (image vector) obtained by the iterative approximation process according to a comparison example, and its update vector.

In the examples as shown in FIGS. 5 and 6, the predetermined number N of the update count is assumed as three, but the count is not limited to this number. It can be set to any predetermined number of counts. For example, there is obtained in advance the number of counts with which the evaluation function $\phi(x)$ or the rate of change of the evaluation function $\nabla\phi(x)$ frequently becomes less than a predetermined value, and thus obtained number of counts can be set as N.

In addition, by way of example, an SD (Standard Deviation) reduction rate is calculated, which is known as one of quantitative values for noise reduction effects of the iterative approximation method, and there is obtained in advance the number of counts with which the SD reduction rate frequently becomes less than a predetermined value, and thus obtained number of counts may also be set as N. As to an SD value that is measured within a small region where pixels values are substantially uniform on an image, the SD reduction rate can be expressed by formula 5, indicating a reduction rate of the SD value of the image generated by the iterative approximation method, with respect to the SD value of the reconstruction image generated by the aforementioned analytical reconstruction method (in the present embodiment, it is equivalent to the initial image $x^{(0)}$).

[Formula 5]

$$SD \text{ REDUCTION RATE} = 1 - \frac{SD \text{ VALUE OF IMAGE GENERATED BY ITERATIVE APPROXIMATION METHOD}}{SD \text{ VALUE OF IMAGE GENERATED BY ANALYTICAL RECONSTRUCTION METHOD}} \quad (5)$$

In other words, the SD reduction rate calculated by formula 5 indicates a reduction ratio of the SD value of the image generated by the first iterative approximation method, with respect to the SD value of the initial image $x^{(0)}$.

When the update count reaches the predetermined number of counts N in step 305, the process goes to step 307, and the SD reduction rate is estimated as to the image at the point of convergence (or the point of asymptotic approaching) according to the iterative approximation method, with respect to the initial image $x^{(0)}$ read in step 301. In formula 4, $\beta_k$ is an optional parameter for determining smoothing strength in the iterative approximation method. Therefore, one-to-one correspondence between the parameter $\beta_k$ and the SD reduction rate can be established, if the following conditions for setting the reduction rate are determined; such as the aforementioned reconstruction parameters (an initial image $x^{(0)}$, and a reconstruction image size, a back-projection phase width, a reconstruction-filter function, and image thickness in body-axis direction, in the iterative approximation method), and values and distributions of the actual measured projection data that varies depending on voltage and current applied to the subject and the X-ray generator. Accordingly, their relationship is put in a tabular form with respect to each of the conditions for setting the reduction rate, thereby allowing calculation of the SD reduction rate, in association with the smoothing strength in the iterative approximation method. In step 307, an estimated value of the SD reduction rate is calculated pixel by pixel, according to the following formula 6.

[Formula 6]

$$\text{ESTIMATED VALUE OF SD REDUCTION RATE} = F(\beta_k) \tag{6}$$

In formula 6, F is a table that is prepared in advance, with respect, to each of the conditions for setting the reduction rate.

There will now be described one example of a method for creating the table F. The conditions for setting the reduction rate are fixed, such as the aforementioned reconstruction parameters (the initial image $x^{(0)}$, and the reconstruction image size, the back-projection phase width, the reconstruction-filter function, and the image thickness in body-axis direction in the iterative approximation method), plotting the SD reduction rate with varying the parameter $\beta_k$, and function fitting is performed according to least squares method. With varying the conditions for setting the reduction rate, for example, with variation of application voltage; such as 80 kV, 100 kV, 120 kV, and 140 kV, functions are derived under the respective conditions.

In those conditions, values and distributions of the actual measured projection data are likely to change, imaging by imaging, there is employed actual measured projection data obtained by imaging a cylindrical water phantom, instead of the subject, and functions are obtained by calculation in advance, as to some phantoms with different diameters. For calculating the estimated value of the SD reduction rate, the function of a phantom having a value of area being the closest to the area of the subject's actual measured projection data, is employed as the table F.

The method for estimating the SD reduction rate in step 307 is not limited to the aforementioned example, but any publicly known methods may be applicable.

When the SD reduction rate of an optional pixel j of the image $x^{(0)}$ is $b_j$, the j-th element of the coupling coefficient $a_g$ is $a_{g,j}$, and the j-th element of the coupling coefficient $a_f$ is $a_{f,j}$, it is possible to assume that the following formulas are established between the two.

[Formula 7]

$$a_{g,j} = h_g(b_j) \ \forall j \tag{7}$$

[Formula 8]

$$a_{f,j} = h_f(b_j) \ \forall j \tag{8}$$

It should be noted that $h_g(b)$ and $h_f(b)$ are functions, each determined uniquely with respect to variable b. Those functions $h_g(b)$ and $h_f(b)$ are calculated in advance according to least squares method, or the like, in such a manner that an approximation error is minimized in the following formula 14, as to clinical data or actual measured projection data regarding an image-quality quantitative phantom, or the like.

Then, coupling coefficients $a_g$ and $a_f$ are calculated or read out, on a pixel basis, the coupling coefficients being associated with the estimated value of the SD reduction rate calculated in step 307, on the basis of the function $h_g(b)$ and $h_f(b)$ or the table, indicating a relationship between the estimated value of the SD reduction rate stored in advance in the storage unit 108, and the coupling coefficients $a_g$ and $a_f$.

Among the difference (update) vectors from the $(N-1)^{th}$ update image to the $N^{th}$ update image, when a vector component originating from data fidelity term is represented as $x_g(N-1, N)$, and a vector component originating from the regularization term is represented as $x_f(N-1, N)$, they are expressed by formulas 10 and 11, according to the aforementioned update formula 1 and the following formula 9, where $n_1=N-1$, $n_2=N$.

[Formula 9]

$$\nabla \Phi(x) = \nabla g(x) + \nabla f(x) \tag{9}$$

[Formula 10]

$$x_g(n_1, n_2) = \sum_{u=n_1}^{n_2} \gamma_g(u), \ \gamma_g(n) = -\lambda_{n-1} D^{-1} \nabla g(x^{(n-1)}) \tag{10}$$

[Formula 11]

$$x_f(n_1, n_2) = \sum_{u=n_1}^{n_2} \gamma_f(u), \ \gamma_f(n) = -\lambda_{n-1} D^{-1} \nabla f(x^{(n-1)}) \tag{11}$$

In step 309, according to formulas 10 and 11, the high-speed arithmetic unit 134 obtains, among the update vectors, the vector component $x_g(N-1, N)$ originating from the data fidelity term, and the vector component $x_f(N-1, N)$ originating from the regularization term, and then, multiplies those components by the coupling coefficients $a_g$ and $a_f$ obtained in step 308, respectively, so as to obtain estimated update vectors. Then, with this result and according to formula 12, an estimated update image $x_\phi^{(N)}=x_\phi(n_1, n_2)$ is obtained; where $n_1=N-1$, $n_2=N$. The estimated update image $x_\phi^{(N)}=x_\phi(n_1, n_2)$ corresponds to a sum of two types of update vectors (estimated update vectors) obtained by multiplication by the coupling coefficients, and updated reconstruction image after $n_1$ iterations.

[Formula 12]

$$x_\phi(n_1, n_2) = a_g^T x_g(n_1, n_2) + a_f^T x_f(n_1, n_2) + x^{(n_1)} \tag{12}$$

In formula 12, "T" in "$a_g^T$" and "$a_f^T$" represents vector transpose.

The aforementioned formula 12 is based on the following assumption. As for the optional value $n_3$, being $n_3 > n_2$, the update vectors for the whole evaluation function, from the $n_1^{th}$ update to the $n_3^{th}$ update, can be expressed by the following formula 13.

[Formula 13]

$$x_\phi(n_1, n_3) = x^{(n_3)} - x^{(n_1)} \qquad (13)$$

Considering that multiple regression analysis is applied, where $x_g(n_1, n_2)$ and $x_f(n_1, n_2)$ in formula 10 and 11 are explanatory variables and $x_F(n_1, n_3)$ in formula 13 is a response variable, it is possible to assume that next formula 14 is established using the coupling coefficients $a_g$ and $a_f$.

[Formula 14]

$$x_\phi(n_1, n_2) \approx a_g^T x_g(n_1, n_2) + a_f^T x_f(n_1, n_2) \qquad (14)$$

According to approximation of formula 14, it is found that the calculation corresponding to $(n_3 - n_2)$ iterations can be omitted. It is to be noted, however, depending on the coupling coefficient, approximation precision of the estimated update vector may be low, and a deviation from $x_\phi(n_1, n_3)$ may be large. Therefore, in order to reduce the approximation error, the image (estimated update image) calculated by the estimated update vector is set as an initial value, and further iterative approximation process (the second iterative approximation process) is performed in the following steps 310 to 315.

Specifically, the high-speed arithmetic unit 134 reads as the initial image from the storage unit 108, thus calculated estimated update image $x_\phi^{(N)}$ (step 310), and generates updated image $x^{(n+1)}$ according to a predetermined update formula (steps 311 and 312). As the update formula, the aforementioned formula 1 may be used, or another formula different from formula 1 may also be applicable. The generated image $x^{(n+1)}$ is stored in the storage unit 108 (step 313). This procedure is repeated until the total update count reaches a predetermined number of times P (steps 314 and 315). The updated image $x^{(P)}$ is stored in the storage unit 108, and it is displayed on the display unit 105 (step 316).

In the present embodiment, according to the iterative approximation method, an image with a high degree of precision, being close to an optimum solution, can be generated at a high speed requiring only a small number of updates.

In the flowcharts as shown in FIG. 3 and FIG. 4, Ordered Subset (OS) algorithm known as an algorithm to speed up the iterative approximation method in image reconstruction, may be applied to formula 2 above, and the evaluation function can be separated into multiple (M) subsets (subset number m) as the following formula:

[Formula 15]

$$\phi(x) = \Sigma_{m=0}^{M-1} \phi_m(x) \qquad (15)$$

[Formula 16]

$$\nabla \phi(x) \approx M \nabla \phi_0(x) \approx \ldots \approx M \nabla \phi_m(x) \approx \ldots \approx M \nabla \phi_{M-1}(x) \qquad (16)$$

In the OS algorithm, instead of minimization of formula 2, minimization of each side in formula 16 is sequentially performed. The calculation of each side in formula 16 is completed by using actual measured projection data of 1/M, and therefore, when all the data is used for updating, update frequency increased by M times can be obtained, compared to formula 1. In this case, the update formula for the $n^{th}$ iteration and the $m^{th}$ subset is expressed by the following formula 17.

[Formula 17]

$$x^{(n,m)} = [x^{(n,m-1)} - \lambda_n D^{-1} \nabla \phi_m(x^{(n,m-1)})]_+ \qquad (17)$$

In formula 17, $x^{(n,m)}$ represents a temporary image vector of the $n^{th}$ iteration and of the $m^{th}$ subset, the value of $x^{(n,m)}$ is equivalent to $x^{(n+1,0)}$, expressing that the image of the $n^{th}$ iteration and of the $m^{th}$ subset is used as the image of the $(n+1)^{th}$ iteration and the $0^{th}$ subset.

When the update formula in formula 17 is used, the reconstruction arithmetic unit 132 divides the actual measured projection data received from the data collection system 129, into M subsets. By way of example, when it is assumed that M=5 for the actual measured projection data of 1,000 views, actual measured projection data is selected every five views in the view direction. Then, the views of 1, 6, 11, . . . , and 996 are allocated to the first (m=1) subset, the view of 2, 7, 12, . . . , and 997 are allocated to the second (m=2) subset, and finally, the views of 5, 10, 15, . . . , 1000 are allocated to the fifth (m=5) subset, whereby, the data is divided into five subsets, each being uniform in the view direction.

In step 301 shown in FIG. 3, the high-speed arithmetic unit 134 reads the reconstruction image generated by the reconstruction arithmetic unit 132, as the initial image $x^{(0)}$. The steps 302, 303, 305, and 306 in FIG. 3 are executed according to the flowchart as shown in FIG. 8.

Figure 8:
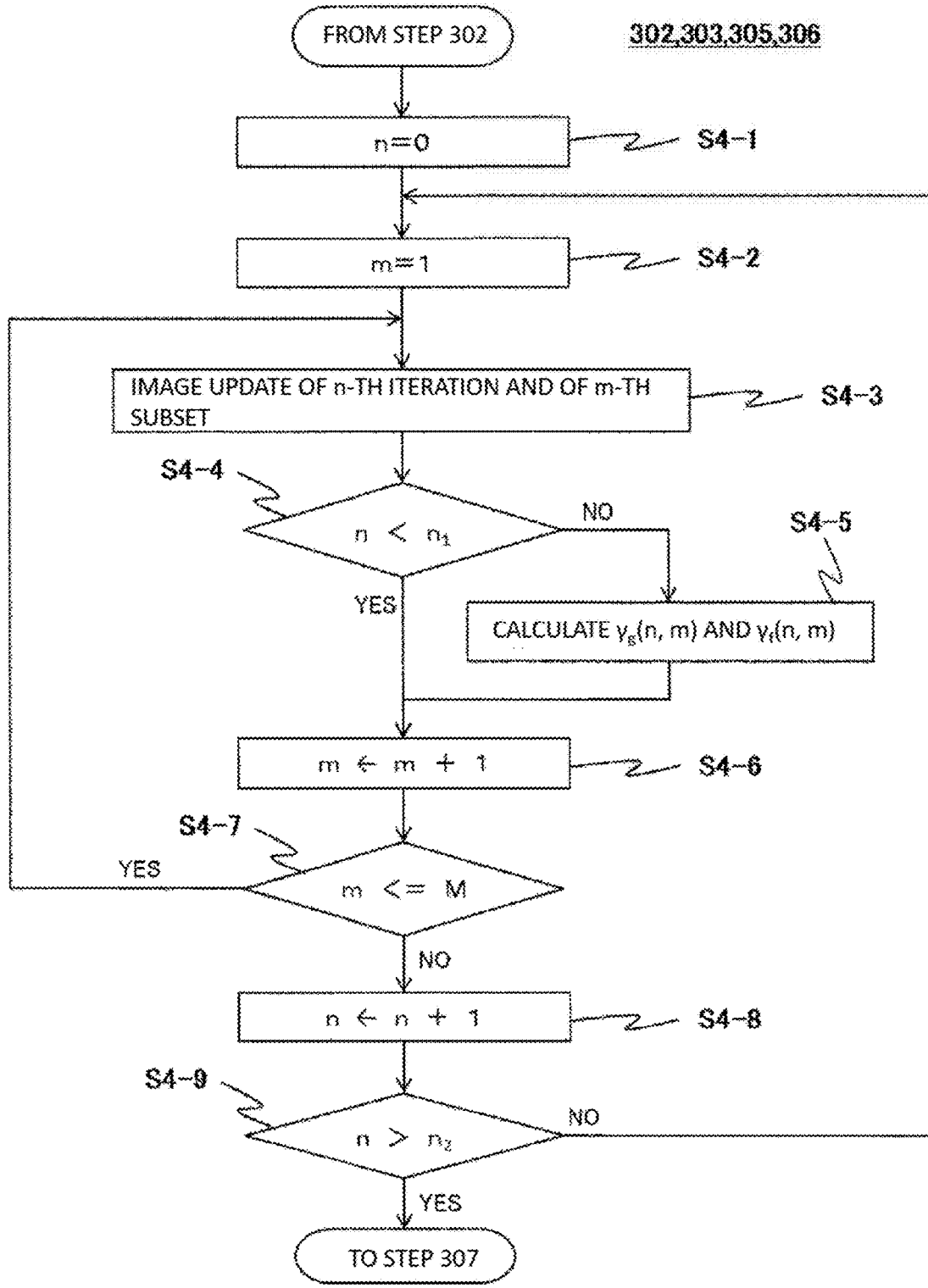
FIG. 8 is a flowchart showing an operation of the first iterative approximation process when a subset of the first embodiment is used.

In the flowchart as shown in FIG. 8, the iteration (update) index n and the subset index m are initialized (n=0, m=1) in steps S4-1 and S4-2. In step S4-3, the $n^{th}$ (=0) update is performed on the image in the $m^{th}$ (=1) subset according to the update formula 17. Then, the index of the subset is incremented by one (step S4-6), and returning to step S4-3, the $n^{th}$ (=0) update is performed on the image in the $m^{th}$ (=2) subset according to the update formula 17. This process is repeated until the index m of the subset reaches M in step S4-7, and when m exceeds M, the process goes to step S4-8, the iteration index n is incremented by one, and the process is further repeated.

When the current iteration index n exceeds the aforementioned $n_1$ ($n_1 = N-1$) in step S4-4, $\gamma_g(n, m)$ and $\gamma_f(n, m)$ are calculated according to formula 18 and formula 19 in step S4-5, and then, they are stored in the storage unit 108. In addition, the subset index m is updated, and image updating is continued (steps S4-6, S4-7, and S4-3).

[Formula 18]

$$x_g(n_1, n_2) = \sum_{u=n_1}^{n_2} \sum_{m=1}^{M} \gamma_g(u, m), \quad \gamma_g(n, m) = -\lambda_n D^{-1} \nabla g(x^{(n,m-1)}) \qquad (18)$$

[Formula 19]

$$x_f(n_1, n_2) = \sum_{u=n_1}^{n_2} \sum_{m=1}^{M} \gamma_f(u, m), \quad \gamma_f(n, m) = -\lambda_n D^{-1} \nabla f(x^{(n,m-1)}) \qquad (19)$$

When the iteration index n incremented in step S4-8 exceeds the aforementioned $n_2$ ($n_2 = N$), the first iterative approximation is terminated, and the process goes to step 307 in FIG. 3. Then, after the high-speed arithmetic unit 134 performs steps 307 and 308 as described above, in step 309, there are calculated from $\gamma_g(n, m)$ and $\gamma_f(n, m)$ obtained in step S4-5, according to formula 18 and formula 19, the vector component $x_g(n_1, n_2)$ originating from the data fidelity term, and the vector component $x_f(n_1, n_2)$ originating from the regularization term, among the update vectors. Then, the estimated update image $x_\phi^{(N)}=x_\phi(n_1, n_2)$ is obtained using the coupling coefficients $a_g$ and $a_f$ obtained in step 308 and according to formula 20.

[Formula 20]

$$x_\phi(n_1, n_2) = a_g^T x_g(n_1, n_2) + a_f^T x_f(n_1, n_2) + x^{(n_1, M)} \quad (20)$$

Figure 9:
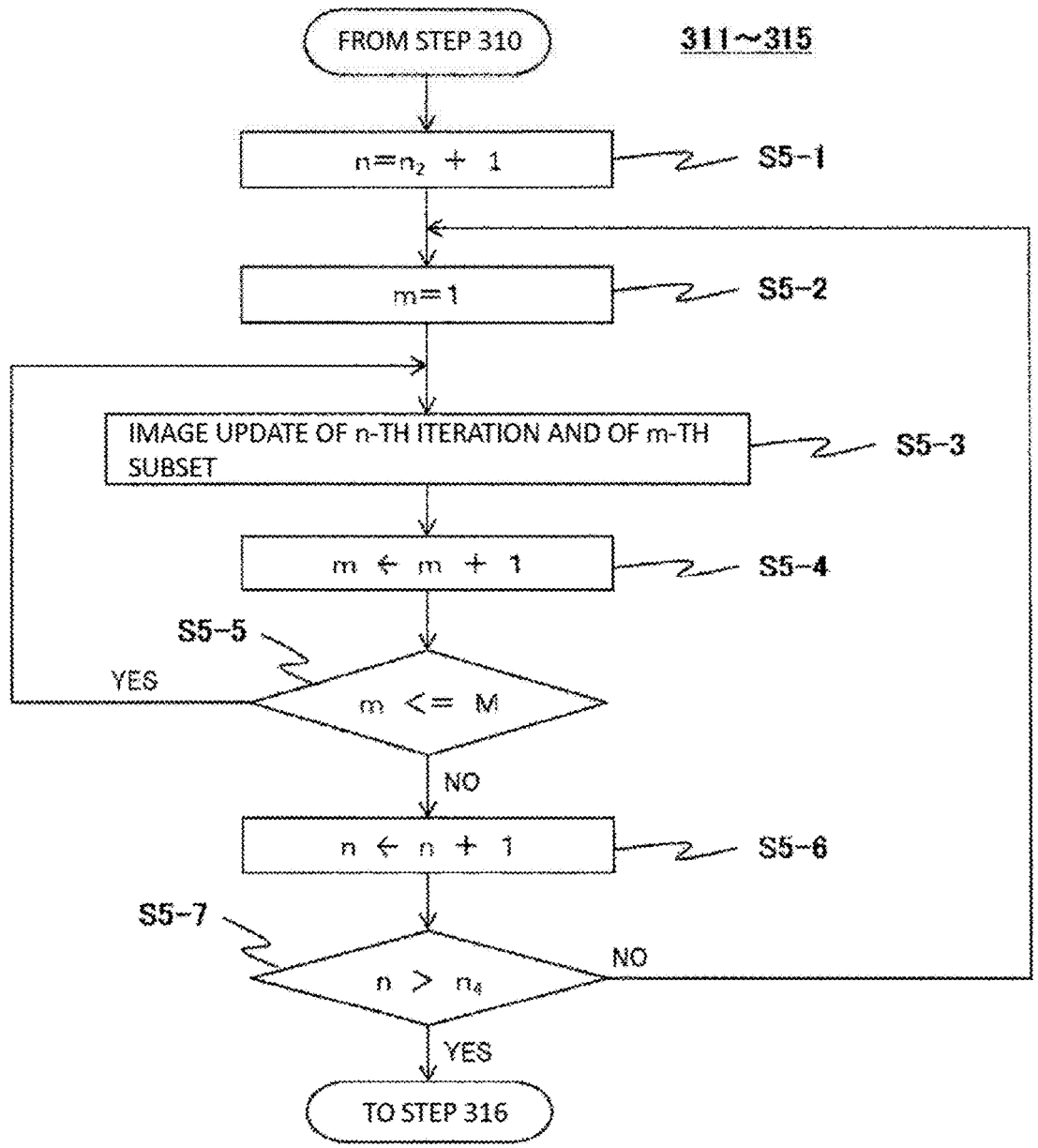
FIG. 9 is a flowchart showing an operation of the second iterative approximation process when the subset of the first embodiment is used.

Setting the estimated update image $x_\phi^{(N)}$ as the initial image (step 310 in FIG. 4), the second iterative approximation process is performed. Specifically, steps 311 to 315 in FIG. 4 are performed according to steps S5-1 to S5-7 in FIG. 9. The iteration index n at the iteration start is assumed as $n_2+1$, and the index n at the iteration end is assumed as $n_4$ ($n_4$=P). Firstly, in steps S5-1 and S5-2, the iteration index n and the subset index m are initialized. In step S5-3, image updating is performed according to the update formula 17. This process is repeated until the subset index m reaches M (steps S5-4 and S5-5).

When the subset index m reaches M after the loop in step S5-5, the iteration index n is updated in step S5-6, and image updating is further performed. In step S5-7, when the iteration index n reaches $n_4$ ($n_4$=P), the iteration is completed, the process goes to step 316, and the reconstruction image is stored and displayed.

In the present embodiment, an example has been described where formulas 1 and 17 are used as the update formulas, respectively in the first and the second iterative approximation processes. However, as far as the aforementioned conditions A and B are satisfied, the update formulas are not limited to formulas 1 and 17. By way of example, it is also possible to employ three types of methods that comprise update formulas of three to five steps using the momentum algorithm, as disclosed in the Non Patent Document 3.

The method as disclosed in the Non Patent Document 3 satisfies the aforementioned conditions A and B, and in the step of image updating, the update vectors of the data fidelity term and the regularization term can be accumulated, respectively. Therefore, this method allows generation of the estimated update image, in the similar manner as the present embodiment.

Second Embodiment

There will now be described a second embodiment.

Similar to the first embodiment, in the second embodiment, after the first iterative approximation process (steps 302 to 305 in FIG. 3) is performed, there are calculated the vector component $x_g(N-1, N)$ originating from the data fidelity term, and the vector component $x_f(N-1, N)$ originating from the regularization term of the difference vector (update vector) of the update images, multiplying those vector components by the coupling coefficients so as to obtain the estimated update vector, and the estimated update image is obtained by calculation using this estimated update vector. At this time, unlike the first embodiment, an update formula satisfying the following conditions A and C is used in the second embodiment, as the update formula of the first iterative approximation process.
A) Evaluation function includes both the data fidelity term and the regularization term; and
C) Upon image updating, the data fidelity term and the regularization term in the condition A are updated alternately (i.e., setting the data fidelity term as a constant, the regularization term is updated, and thereafter, setting the regularization term as a constant, the data fidelity term is updated).

Specifically, as the update formula satisfying the conditions A and C, the update formula described in the Non Patent Document 4 is employed.

The update formula described in the Non Patent Document 4 will now be explained. The update formula of the present embodiment introduces a new variable as the data fidelity term in the optimization of the aforementioned formulas 2 to 4, performing formulation using a relational expression of thus introduced variable as a constraint, and then, optimization is performed.

Firstly, Ax in formula 3 is replaced by a new variable u, and formula 3 is rewritten as the next formula 21.

[Formula 21]

$$g(x) = \hat{g}(u) = \|u - y\|_W \quad (21)$$

By using this formula 21, formula 22 substitutes for the aforementioned formula 2.

[Formula 22]

$$\phi(x, u) = \hat{g}(u) + f(x) \text{ subject to } u = Ax \quad (22)$$

A punishment parameter $\rho$ is introduced into formula 22, and the Augmented Lagrangian method is applied. Then, update formulas for updating the two variables x and u alternately, can be obtained according to formulas 23.1, 23.2, and 23.3 as shown in the following.

[Formula 23]

$$\begin{cases} x^{(n)} = \operatorname{argmin}_x \{f(x) + \frac{\rho}{2}\|Ax - u^{(n-1)} - d^{(n-1)}\|_2^2\} & (23.1) \\ u^{(n)} = \operatorname{argmin}_x \{\hat{g}(u) + \frac{\rho}{2}\|Ax^{(n)} - u - d^{(n-1)}\|_2^2\} & (23.2) \\ d^{(n)} = d^{(n-1)} - Ax^{(n)} + u^{(n)} & (23.3) \end{cases}$$

On the other hand, when the OS algorithm is applied to the data fidelity term only, the next formulas 24 and 25 are obtained.

[Formula 24]

$$g(x) = \Sigma_{m=0}^{M-1} g_m(x) \quad (24)$$

[Formula 25]

$$\nabla g(x) \approx M\nabla g_0(x) \approx \ldots \approx M\nabla g_m(x) \approx \ldots \approx M\nabla g_{M-1}(x) \quad (25)$$

By applying the OS algorithm of formulas 24 and 25 to formula 23.1, the update formulas of 26.1, 26.2, and 26.3 are obtained as the following.

[Formula 26]

$$\begin{cases} s^{(n,m)} = \rho M \nabla g_m(x^{(n,m-1)}) + (1-\rho)b^{(n,m-1)} & (26.1) \\ x^{(n,m)} \in \operatorname{prox}_{\frac{t}{\rho}f}\left(x^{(n,m-1)} - \frac{t}{\rho}s^{(n,m)}\right) & (26.2) \\ b^{(n,m)} = \frac{\rho}{\rho+1}M\nabla g_m(x^{(n,m)}) + \frac{1}{\rho+1}b^{(n,m-1)} & (26.3) \end{cases}$$

In formulas 23.1 to 23.3, and in formulas 26.1 to 26.3, an optional constant $L > \|A\|_2^2$ and $t = 1/L$.

Formulas 26.1, 26.2, and 26.3 indicate a series of update procedures of the $n^{th}$ iteration and of the $m^{th}$ subset. However, $x^{(n, m)}$ in formula 26.2 may be calculated iteratively, depending on the property of the regularization term f(x). Therefore, formula 26.2 utilizes a publicly known Fast Iterative Shrinkage-Thresholding Algorithm (FISTA, Non Patent Document 2), so as to solve a partial problem where $x^{(n, m)}$ is calculated iteratively.

Also in the second embodiment, similar to formulas 18 and 19 in the first embodiment, it is necessary to calculate the update vector originating from the data fidelity term, and the update vector originating from the regularization term in step 309 of FIG. 3. Therefore, the aforementioned partial problem of formula 26.2 is rewritten by the next formula 27.

[Formula 27]

$$x^{(n,m)} = \arg\min_z \left\{ \frac{t}{\rho} f(z) + \frac{1}{2} \left\| z - \left( x^{(n,m-1)} - \frac{t}{\rho} s^{(n,m)} \right) \right\|_2^2 \right\} \quad (27)$$

In formula 27, when the regularization term f(z)=0, formula 27 is represented by formula 28.

[Formula 28]

$$x^{(n,m)}|_{f(z)=0} = x^{(n,m-1)} - \frac{t}{\rho} s^{(n,m)} \quad (28)$$

Therefore, the update vector $\gamma_g(n, m)$ originating from the data fidelity term of the $n^{th}$ iteration and of the $m^{th}$ subset is expressed by the next formula 29.

[Formula 29]

$$\gamma_g(n, m) = -\frac{t}{\rho} s^{(n,m)} \quad (29)$$

On the other hand, the update vector $\gamma_f(n, m)$ originating from the regularization term of the $n^{th}$ iteration and of the $m^{th}$ subset is expressed by the following formula.

[Formula 30]

$$\gamma_f(n, m) = x^{(n,m)} + \frac{t}{\rho} s^{(n,m)} \quad (30)$$

In addition, it is further possible to accumulate the update vector $\gamma_f(n, m)$ in the iteration process of formula 27. Here, the update index of the partial problem of formula 27 is represented as ω, and a temporary image is represented as $z^{(\omega)}$. In addition, when the iteration count at the time of convergence is represented as •, and an initial value of the iteration is represented as $z^{(0)} = x^{(n, m-1)} - t/\rho s^{(n, m)}$, $\gamma_f(n, m)$ is expressed by the following formula 31.

[Formula 31]

$$\gamma_f(n, m) = \sum_{\omega=1}^{\bullet} z^{(\omega)} - z^{(\omega-1)} \quad (31)$$

In step 309, $\gamma_g(n, m)$ in formula 29 is substituted for $\gamma_g(n, m)$ in formula 18, and $\gamma_f(n, m)$ in formula 30 or in formula 31 is substituted for $\gamma_f(n, m)$ in formula 19, whereby the vector components $x_g(n_1, n_2)$ and $x_f(n_1, n_2)$ of the update vector can be obtained by calculation.

As described above, even when employing the iterative approximation method where the data fidelity term and the regularization term are alternately updated, it is also possible to easily separate the update vectors originating respectively from those terms, by focusing on the update components of the respective terms alternately in the update formula.

In the second embodiment, other steps in FIG. 3 are the same as the processing operations using the subset in the first embodiment, and therefore, they will not be described redundantly. Similarly, the update formula as described in the present embodiment is also applicable to the second iterative approximation process as shown in FIG. 4.

It should be noted that as far as the aforementioned conditions A and C are satisfied, it is also possible to employ another update formula, instead of the update formula as described in the present embodiment.

Third Embodiment

There will now be described a third embodiment.

In the third embodiment, similar to the second embodiment, there is employed an update formula that satisfies the aforementioned conditions A and C, and introduces a new variable to the regularization term.

There will now be described the update formula used in the third embodiment.

In the present embodiment, the update formula satisfies the conditions A and C and employs a non-differentiable continuous function as the regularization term. Total Variation (TV) represents the continuous function that is non-differentiable, and it is expressed by the following formulas 32 to 35.

[Formula 32]

$$f(x) = \beta \psi(\nabla_v x, \nabla_h x) \quad (32)$$

[Formula 33]

$$\psi(\nabla_v x, \nabla_h x) = \|\nabla_v x\|_1 + \|\nabla_h x\|_1 \quad (33)$$

[Formula 34]

$$\psi(\nabla_v x, \nabla_h x) = \sum_{j=1}^{J} \sqrt{([\nabla_v x]_j)^2 + ([\nabla_h x]_j)^2} \quad (34)$$

[Formula 35]

$$[\nabla_v x]_j = x_{p+1,q} - x_{p,q}, \; [\nabla_h x]_j = x_{p,q+1} - x_{p,q} \quad (35)$$

In formula 35, as for an optional slice of a three-dimensional image, vertical and horizontal indexes p={1, . . . , P} and q={1, . . . , Q} of the image, and pixel index j, are associated with one another according to the following formula.

[Formula 36]

$$j = \varsigma(p, q) = p + Pq \quad (36)$$

Formula 33 and Formula 34 are referred to as anisotropic TV and isotropic TV, respectively, and they are selected and employed depending on usage.

Here, $\nabla_v x$ and $\nabla_h x$ in formula 33 are replaced by new variables $v_v$ and $v_h$, and it is rewritten as the following formula 37.

[Formula 37]

$$\psi(v_v, v_h) = \|v_v\|_1 + \|v_h\|_1 \tag{37}$$

Following formula 38 is obtained from formula 2, formula 32, and formula 37.

[Formula 38]

$$\phi(x, v_v, v_h) = g(x) + \beta \psi(v_v, v_h) \text{ subject to } v_v = \nabla_v x, v_h = \nabla_h x \tag{38}$$

In addition, punishment parameter $\rho$ is introduced, and following update formulas 39 and 40 are obtained, by applying the Split Bregman method.

[Formula 39]

$$(x^{(n)}, v_v^{(n)}, v_h^{(n)}) = \min_{x, v_v, v_h} g(x) + \beta \psi(v_v, v_h) + \tag{39}$$
$$\frac{\rho}{2}\|v_v - \nabla_v x - d_v^{(n-1)}\|_2^2 + \frac{\rho}{2}\|v_h - \nabla_h x - d_h^{(n-1)}\|_2^2$$

[Formula 40]

$$d_v^{(n)} = d_v^{(n-1)} + \nabla_v x^{(n)} - v_v^{(n)}, \; d_h^{(n)} = d_h^{(n-1)} + \nabla_h x^{(n)} - v_h^{(n)} \tag{40}$$

As for formula 38, when the three variable vectors are minimized alternately, the following formulas 41.1 to 41.3 are obtained.

[Formula 41]

$$\begin{cases} x^{(n)} = \{x_{1,1}^{(n)}, \ldots, x_{p,q}^{(n)}, \ldots, x_{P,Q}^{(n)}\} & (41.1) \\ v_v^{(n)} = \text{shrink}(\nabla_v x^{(n-1)} + d_v^{(n-1)}, 1/\rho) & (41.2) \\ v_h^{(n)} = \text{shrink}(\nabla_h x^{(n-1)} + d_h^{(n-1)}, 1/\rho) & (41.3) \end{cases}$$

Here, $x^{(n)}_{p,q}$ in formula 41.1 is expressed by formula 42, according to the Gauss-Seidel method.

[Formula 42]

$$x_{p,q}^{(n)} = \frac{\rho}{2/\beta + 4\rho} \tag{42}$$
$$(x_{p+1,q}^{(n-1)} + x_{p-1,q}^{(n-1)} + x_{p,q+1}^{(n-1)} + x_{p,q-1}^{(n-1)} + v_{v,p-1,q}^{(n-1)} - v_{v,p,q}^{(n-1)} + v_{h,p,q-1}^{(n-1)} -$$
$$v_{h,p,q}^{(n-1)} - d_{v,p-1,q}^{(n-1)} + d_{v,p,q}^{(n-1)} - d_{h,p,q-1}^{(n-1)} + d_{h,p,q}^{(n-1)}) + \frac{1/\beta}{1/\beta + 2\rho} y_{p,q}$$

A shrink function of formula 41.2 and formula 41.2 is expressed by the following formula 43.

[Formula 43]

$$\text{shrink}(\omega, \tau) = \max(|\omega| - \tau, 0) \cdot \text{sgn}(\omega) \tag{43}$$

Among the formulas as described above, formula 39, formula 40, formula 41.1, formula 41.2, and formula 41.3 are used as the update formulas.

A concept of the present embodiment is the same as that of the first and the second embodiments, and an update vector originating from the data fidelity term and an update vector originating from the regularization term are obtained by calculation. Firstly, for ease of explanation, the right side of formula 41.1 is partially differentiated with respect to x, and the following formula is obtained.

[Formula 44]

$$\nabla \phi(x, v_v, v_h) = \nabla g(x) - \frac{\rho}{2}(v_v - \nabla_v x - d_v^{(n-1)}) - \frac{\rho}{2}(v_h - \nabla_h x - d_h^{(n-1)}) \tag{44}$$

By contrasting with formula 44, the update vector $\gamma_g(n)$ originating from the data fidelity term of the $n^{th}$ iteration in formula 42 is expressed by the following formulas 45 and 46.

[Formula 45]

$$\gamma_g(n) = \{\bar{\gamma}_{g,1,1}(n), \ldots, \bar{\gamma}_{g,p,q}(n), \ldots, \bar{\gamma}_{g,P,Q}(n)\} \tag{45}$$

[Formula 46]

$$\bar{\gamma}_{g,p,q}(n) = \frac{1/\beta}{1/\beta + 2\rho} y_{p,q} \tag{46}$$

On the other hand, the update vector $\gamma_f(n)$ originating from the regularization term of the $n^{th}$ iteration is expressed by the next formulas 47 and 48.

[Formula 47]

$$\gamma_f(n) = \{\bar{\gamma}_{f,1,1}(n), \ldots, \bar{\gamma}_{f,p,q}(n), \ldots, \bar{\gamma}_{f,P,Q}(n)\} \tag{47}$$

[Formula 48]

$$\bar{\gamma}_{f,p,q}(n) = \tag{48}$$
$$\frac{\rho}{2/\beta + 4\rho}(x_{p+1,q}^{(n-1)} + x_{p-1,q}^{(n-1)} + x_{p,q+1}^{(n-1)} + x_{p,q-1}^{(n-1)} + v_{v,p-1,q}^{(n-1)} - v_{v,p,q}^{(n-1)} +$$
$$v_{h,p,q-1}^{(n-1)} - v_{h,p,q}^{(n-1)} - d_{v,p-1,q}^{(n-1)} + d_{v,p,q}^{(n-1)} - d_{h,p,q-1}^{(n-1)} + d_{h,p,q}^{(n-1)})$$

Here, assuming M=1, formula 44 is substituted for $\gamma_g(n, m)$ of formula 17, and formula 47 is substituted for $\gamma_f(n, m)$ of formula 19, thereby obtaining by calculation, the vector components $x_g(n_1, n_2)$ and $x_f(n_1, n_2)$ of the update vectors.

As described above, even when employing the iterative approximation method where the data fidelity term and the regularization term are alternately updated, it is also possible to easily separate the update vectors originating respectively from those terms, by focusing alternately on the update components of the respective terms in the update formula.

It is to be noted that in the present embodiment, there is shown the update formula that uses the algorithm as described in the Non Patent Document 5. However, the update formula is not limited to the aforementioned formula, as far as the conditions A and C above are satisfied.

By way of example, in the Non Patent Document 6, there are described a method for applying the Alternating Direction Method of Multipliers (ADMM) algorithm and an algorithm for applying the Split Bregman method, after performing variable separation not only of the data fidelity term, but also of the regularization term. In addition, also in the Non Patent Document 7, there is described an algorithm for performing variable separation of both the data fidelity term and the regularization term. It is further possible to employ the update formula on the basis of those methods above.

Fourth Embodiment

There will now be described a fourth embodiment.

In the embodiments 1 to 3, as shown in FIG. 3 and FIG. 4, it is configured such that iterations of predetermined N times are perforated in the first iterative approximation process (steps 302 to 306), and iterations of predetermined (P-N) times are performed in the second iterative approximation process (steps 311 to 315). However, the present invention is not limited to this configuration.

By way of example, the high-speed arithmetic unit 134 may be configured such that it accepts from an operator, a value of total count P of the first and second iterative approximation processes.

In this case, as for the iteration counts N and (P-N), respectively of the first iterative approximation process and the second iterative approximation process, if the former count is large and the latter count is small, the precision level of the estimated update image becomes substantially higher. However, there is a possibility that sufficient asymptotic approach to an optimum solution cannot be achieved if the iteration count of the second iterative approximation process is considerably small.

On the other hand, if the latter count is large and the former count is small, sufficient precision of the estimated update image cannot be obtained, and an effect of speeding up according to the present invention may not be obtained sufficiently. In view of both situations above, it is desirable to determine in advance by experiment or by calculation, a relationship between P and N, so that the iteration counts are balanced between the first iterative approximation process and the second iterative approximation process. Thus obtained relationship between P and N may be stored in the form of table or as a function, in the storage unit 108. Accordingly, the high-speed arithmetic unit 134 can use a value of N, in association with P that is set by the operator, by reading the value from the table, or obtaining by calculation.

Fifth Embodiment

There will now be described the fifth embodiment.

Figure 10:
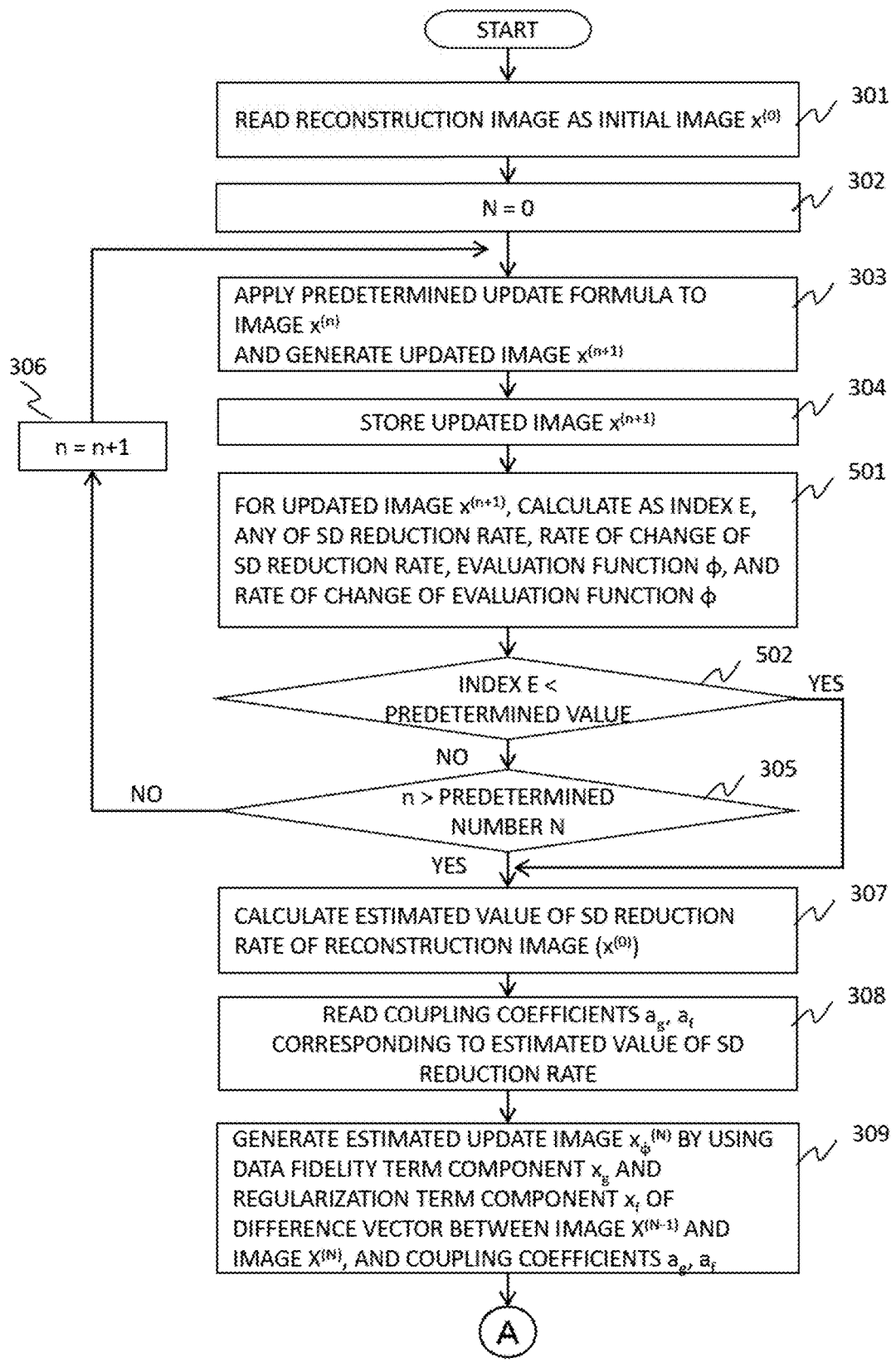
FIG. 10 is a flowchart showing an operation of the high-speed computing device of the CT device according to the fifth embodiment.

In the present embodiment, as shown in FIG. 10, in the first iterative approximation process (steps 302 to 306) of FIG. 3, prior to step 305 determining whether the iteration count reaches the predetermined number N, steps 501 and 502 are inserted for calculating an index E, so as to determine whether the updated image $x^{(n+1)}$ approaches the optimum solution to the extent appropriate for generating the estimated update image $x_\phi^{(N)}$ in step 309. This point is different from the first embodiment. The other steps in the flowchart of FIG. 10 are the same as those in FIG. 3, and thus they will not be described redundantly.

Any of the followings may be used as the index E; SD reduction rate of the entire updated image $x^{(n+1)}$ or SD reduction rate on the periphery of a focused pixel, the rate of change (e.g., the amount of change) of the SD reduction rate between a current update image $x^{(n+1)}$ and a previous update image $x^{(n)}$, a value of the evaluation function $\phi$ of the updated image $x^{(n+1)}$, the rate of change (e.g., the amount of change) of the values of evaluation function $\phi$ between the current update image $x^{(n+1)}$ and the previous update image $x^{(n)}$.

In step 501, the high-speed arithmetic unit 134 obtains by calculation using a predetermined formula, the SD reduction rate or the evaluation function $\phi$ as to the updated image $x^{(n+1)}$ generated in step 304, and stores the result in the storage unit 108. If the amount of change is used as the index E, a difference from the previously stored SD reduction rate or value of the evaluation function $\phi$ is calculated. As the predetermined formula, formulas 49 and 50 may be used, for instance.

[Formula 49]

$$SD \text{ REDUCTION RATE} = 1 - \frac{SD \text{ VALUE OF UPDATED IMAGE } X^{(n+1)}}{SD \text{ VALUE OF INITIAL IMAGE } X^{(0)}} \quad (49)$$

[Formula 50]

$$\Phi(x^{(n+1)}) = g(x^{(n+1)}) + f(x^{(n+1)}) \quad (50)$$

In step 502, the index E calculated in step 501 is compared with a predetermined value, and when the index E is smaller than the predetermined value, it is determined that the updated image $x^{(n+1)}$ approaches the optimum solution to the extent appropriate for generating the estimated update image $x_\phi^{(N)}$, and the iteration of the first iterative approximation process is terminated, then proceeding with step 307.

Accordingly, the high-speed arithmetic unit 134 ends the first iterative approximation process, before the iteration count n reaches N, enabling to generate the estimated update image $x_\phi^{(N)}$ in steps 307 to 309.

On the other hand, in step 502, if the index E is not smaller than the predetermined value, the process goes to step 305, and if the iteration count n does not exceed N, the iteration process is continued. If the iteration count n exceeds N before the index E becomes smaller than the predetermined value, then the process goes to step 307, and the iteration process is terminated. Therefore, an upper limit of the iteration count n can be maintained to N times.

As described above, in the present embodiment, it is possible to determine whether the iteration process should be continued or not, according to the state of the updated image. Therefore, this allows the first iterative approximation process to generate the estimated update image, at a higher speed without performing unnecessary iteration process.

Figure 11:
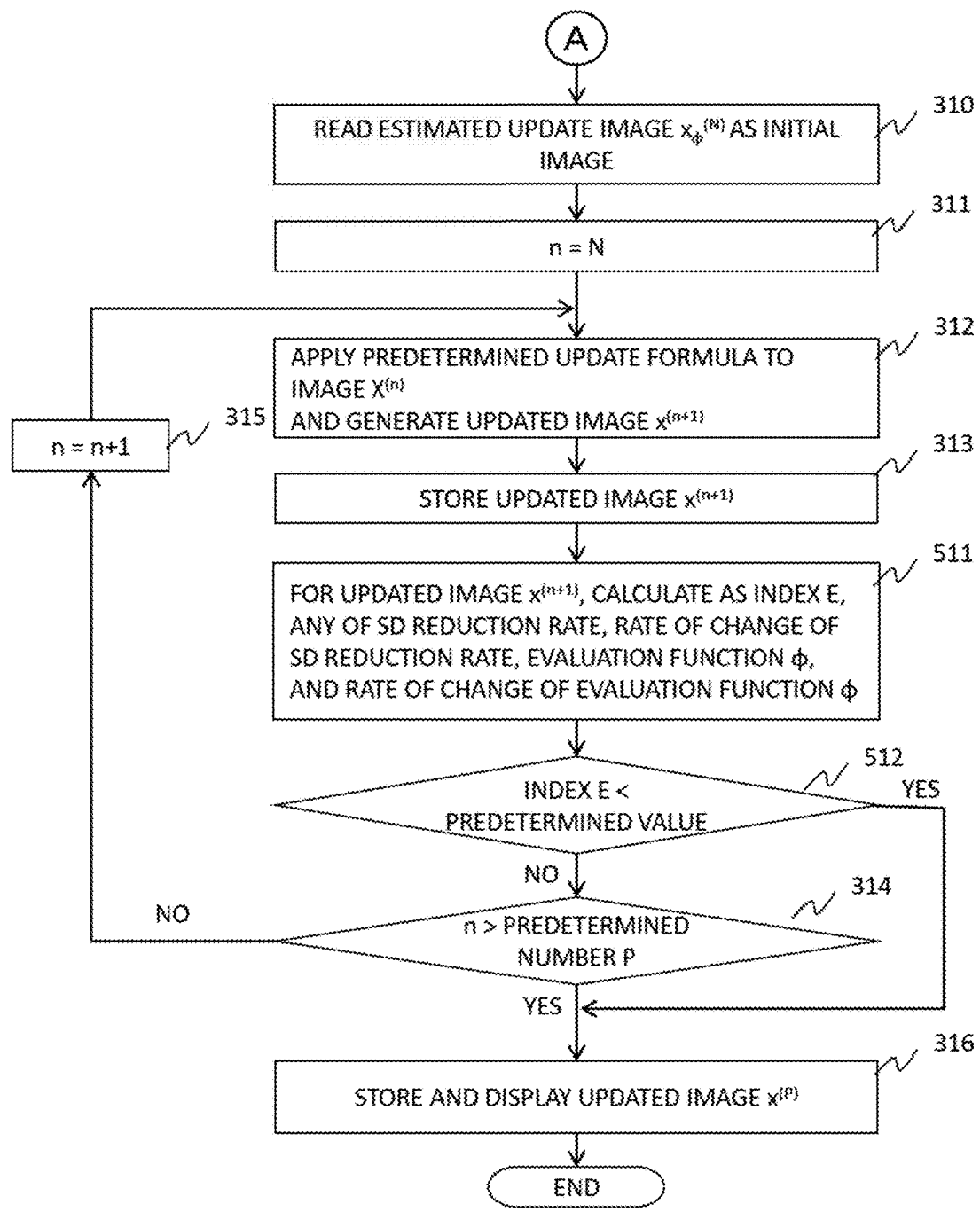
FIG. 11 is a flowchart showing an operation of the high-speed computing device of the CT device according to the fifth embodiment.

Similarly, as shown in the flowchart of FIG. 11, also in the second iterative approximation process (steps 311 to 315) of FIG. 4, it is possible to insert steps 511 and 512 for calculating the index E, so as to determine whether the updated image $x^{(n+1)}$ approaches the optimum solution, prior to step 314 for determining whether the iteration count reaches the predetermined number P. The other steps in the flowchart of FIG. 11 are the same as those in FIG. 4, and they will not be described redundantly.

In step 511, similar to step 501, any of the index E is calculated for the updated image $x^{(n+1)}$ that is generated in step 312.

In step 512, the index E calculated in step 501 is compared with a predetermined value, and when the index E is smaller than the predetermined value, it is determined as sufficiently approaching the optimum value. Then, iteration of the second iterative approximation process is terminated and the process goes to step 316. It is to be noted that a value of the predetermined value for determining the index E in step 512 may be different from the predetermined value used in step 502.

Accordingly, the high-speed arithmetic unit 134 is allowed to terminate the first iterative approximation process before the iteration count, n reaches P.

On the other hand, in step 502, in the case where the index E is not smaller than the predetermined value, the process goes to step 314, and if the iteration count n does not exceed P, the iteration process is continued. In the case where the iteration count n exceeds P before the index E obtained in step 511 becomes smaller than the predetermined value, the process goes to step 316, and the iteration process is terminated. Therefore, it is possible to maintain the upper limit of the iteration count n to P, as a total of the first and the second iterative approximation processes.

As described above, also in the second iterative approximation process, it is possible to determine whether or not the iteration process should be continued, according to the state of the updated image, and an image asymptotically approaching the optimum solution can be generated at high speed, without performing unnecessary iterations in the second iterative approximation process.

In the aforementioned embodiments, descriptions have been made with regard to a CT device, but the process of the high-speed arithmetic unit 134 of the present embodiment may be used for generating an image in other imaging systems, such as an MRI device.

It should be noted that in the first to the third embodiments, it has been described that the evaluation function comprises two terms; the data fidelity term and the regularization term, but it is also possible to apply three or more estimated update vectors to the evaluation function that comprises three or more terms.

DESCRIPTION OF SYMBOLS 101 scanner, 102 bed, 103 input unit, 104 arithmetic unit, 105 display unit, 108 storage unit, 111 X-ray generator, 121 detector, 132 reconstruction arithmetic unit, 134 high-speed arithmetic unit

What is claimed is:

1. An image computing device comprising,
a first iterative approximation processor configured to receive a specified tomographic image of a subject, and to perform a process two or more times, where an update process is performed according to the iterative approximation method using the specified tomographic image as an initial image, and an update image is obtained,
an estimated update image generator configured to generate an estimated update vector obtained by multiplying an update vector by a predetermined coefficient, the update vector corresponding to a difference between the update images of the update process performed twice, generated by the first iterative approximation processor, and to generate an estimated update image by using the estimated update vector, and
a second iterative approximation processor configured to repeat a process where the update process is performed according to the iterative approximation method and an update image is obtained, using the estimated update image as a new initial image, thereby generating a tomographic image of the subject.

2. The image computing device according to claim 1, wherein,
the estimated update image generator separates the update vector into two or more vector components, multiplies the two or more vector components by coefficients, different respectively, and adds the vector components, thereby generating the estimated update vector.

3. The image computing device according to claim 2, wherein,
the first iterative approximation processor uses a formula including a data fidelity term and a regularization term, as an update formula used in the update process according to the iterative approximation method, and
the estimated update image generator separates the update vector into the vector component originating from the data fidelity term and the vector component originating from the regularization term.

4. The image computing device according to claim 1, wherein,
the estimated update image generator calculates an index from a pixel value of the specified tomographic image, obtains a coefficient associated with the index, and multiplies the update vector by thus obtained coefficient.

5. The image computing device according to claim 4, wherein,
the index is an estimated value of an SD (standard deviation) reduction rate of a pixel value in the specified tomographic image.

6. The image computing device according to claim 4, wherein,
the estimated update image generator has a function or a table showing a relationship between the index being predetermined and a value of the coefficient, and the value of the coefficient is obtained, in association with the index being calculated, on the basis of the function or the table.

7. The image computing device according to claim 1, wherein,
the first iterative approximation processor performs the update process for a predetermined number of counts.

8. The image computing device according to claim 1, wherein,
the first iterative approximation processor calculates a specified index as to the update image, and when the specified index becomes less than or equal to a predetermined value, the update process is terminated.

9. The image computing device according to claim 8, wherein,
the specified index includes any of an SD reduction rate of a pixel value in the update image, the rate of change of the SD reduction rate, a value of a specified evaluation function of the pixel value in the update image, and the rate of change of the value of the evaluation function.

10. An image computing method comprising,
repeating a process two or more times, where an update process is performed according to an iterative approximation method using a tomographic image as an initial image and an update image is obtained,
generating an estimated update vector obtained by multiplying an update vector by a specified coefficient, the update vector corresponding to a difference between the update images that are obtained by the update process performed twice, and generating an estimated update image by using this estimated update vector, and
repeating the process where the update process is performed according to the iterative approximation method and an update image is obtained, using the estimated update image as a new initial image, thereby generating a tomographic image of the subject.

11. A tomography scanner comprising,
an imaging part configured to image a tomographic image of a subject, and an image computing device configured to generate a second tomographic image of the subject, by using the tomographic image obtained by the imager, wherein,
the image computing device corresponds to the image computing device according to claim 1.

* * * * *